US009750955B2

(12) United States Patent
McNutt et al.

(10) Patent No.: US 9,750,955 B2
(45) Date of Patent: Sep. 5, 2017

(54) DOSE COMPUTATION FOR RADIATION THERAPY USING HETEROGENEITY COMPENSATED SUPERPOSITION

(71) Applicant: The Johns Hopkins University, Baltimore, MD (US)

(72) Inventors: Todd McNutt, Severna Park, MD (US); Robert A. Jacques, Burnaby (CA)

(73) Assignee: The Johns Hopkins University, Baltimore, MD (US)

( * ) Notice: Subject to any disclaimer, the term of this patent is extended or adjusted under 35 U.S.C. 154(b) by 347 days.

(21) Appl. No.: 14/346,949

(22) PCT Filed: Oct. 1, 2012

(86) PCT No.: PCT/US2012/058345
§ 371 (c)(1),
(2) Date: Mar. 24, 2014

(87) PCT Pub. No.: WO2013/049839
PCT Pub. Date: Apr. 4, 2013

(65) Prior Publication Data
US 2014/0235923 A1      Aug. 21, 2014

Related U.S. Application Data

(60) Provisional application No. 61/540,773, filed on Sep. 29, 2011.

(51) Int. Cl.
*A61N 5/10*      (2006.01)
*G06F 19/00*     (2011.01)

(52) U.S. Cl.
CPC .......... *A61N 5/1031* (2013.01); *A61N 5/103* (2013.01); *A61N 5/1048* (2013.01);
(Continued)

(58) Field of Classification Search
CPC ........ A61N 5/10; A61N 5/103; A61N 5/1031; A61N 5/1032; A61N 5/1036;
(Continued)

(56) References Cited

U.S. PATENT DOCUMENTS 5,602,892 A    2/1997   Llacer
6,301,329 B1  10/2001   Surridge
(Continued)

FOREIGN PATENT DOCUMENTS

WO   WO-2006138513 A1   12/2006
WO   WO-2008013956 A1    1/2008
WO   WO-2009137794 A2   11/2009

OTHER PUBLICATIONS

Mackie et al., Proceedings of the 1996 AAPM Summer School, 1996.
(Continued)

*Primary Examiner* — Anastasia Midkiff
(74) *Attorney, Agent, or Firm* — Venable LLP; Henry J. Daley; Laura G. Remus

(57) ABSTRACT

A system for radiation therapy includes a radiation planning system. The radiation planning system includes a data processor that is adapted to receive information concerning an intended radiation treatment region of a body, receive a calculated initial energy released per unit mass for a plurality of locations within the body, compute a radiation dose at a plurality of locations within the radiation treatment region based on the calculated initial energy released per unit mass and including radiation dose contributions due to scattering from other locations within the body, and determine radiation therapy parameters for providing radiation treatment to the intended radiation treatment region based on the radiation dose computed at the plurality of locations within the radiation treatment region. Including radiation dose contri-
(Continued)

butions due to scattering from other locations within the body take into account density discontinuities in the body.

27 Claims, 42 Drawing Sheets

(52) U.S. Cl.
CPC ......... *A61N 5/1067* (2013.01); *A61N 5/1071* (2013.01); *A61N 5/1075* (2013.01); *A61N 2005/1032* (2013.01); *G06F 19/3481* (2013.01)

(58) Field of Classification Search
CPC .. A61N 5/1039; A61N 5/1048; A61N 5/1064; A61N 5/1065; A61N 5/1067; A61N 5/1071; A61N 5/1075; A61N 2005/1032; G06F 19/30; G06F 19/34; G06F 19/3481; G06T 7/0012
See application file for complete search history.

(56) References Cited

U.S. PATENT DOCUMENTS

| | | | | |
|---|---|---|---|---|
| 6,636,622 | B2* | 10/2003 | Mackie | A61N 5/1048 378/145 |
| 8,325,878 | B2* | 12/2012 | McNutt | A61N 5/1031 378/65 |
| 2004/0096033 | A1 | 5/2004 | Seppi et al. | |
| 2006/0033044 | A1 | 2/2006 | Gentry et al. | |
| 2008/0091388 | A1 | 4/2008 | Failla et al. | |
| 2008/0292055 | A1* | 11/2008 | Boone | G01T 1/02 378/97 |
| 2011/0051893 | A1 | 3/2011 | McNutt et al. | |
| 2011/0158386 | A1* | 6/2011 | Payne | A61B 5/4872 378/54 |
| 2014/0094642 | A1* | 4/2014 | Fuji | A61N 5/1031 600/1 |

OTHER PUBLICATIONS

Ahnesjo et al., Acta. Oncol., 26, 49-56, 1987.
Ahnesjo et al., Phys. Med. Biol. 44, R99-R155 1999.
Ahnesjo, Med. Phys. 16, 577-92, 1989.
Amanatides et al., Eurographics'87, Conference Proceedings, 1987.
Liu et al., Med. Phys. 24, 1729-1741, 1997.
Lu et al., Phys. Med. Biol. 50, 655-680, 2005.
Mackie et al., Use of Comp. In Rad. Ther., 107-110 1987.
Mackie et al., Phys. Med. Biol. 33, 1-20,1988.
Mackie et al., Med. Phys. 12, 188-196, 1985.
Mohan et al., Med. Phys. 12, 592-597, 1985.
Otto, Med. Phys. 35, 310-317, 2008.
Papanikolaou et al., Med. Phys. 20, 1327-1336, 1993.
Williams, SIGGRAPH Comput. Graph. 17, 3, 1-11, 1983.
Yan et al., Phys. Med. Biol. 42, 123-132, 1997.
Yu, Phys. Med. Biol. 40, 1435-1449, 1995.
International Search Report and Written Opiinion of PCT/US2012/058345.

* cited by examiner

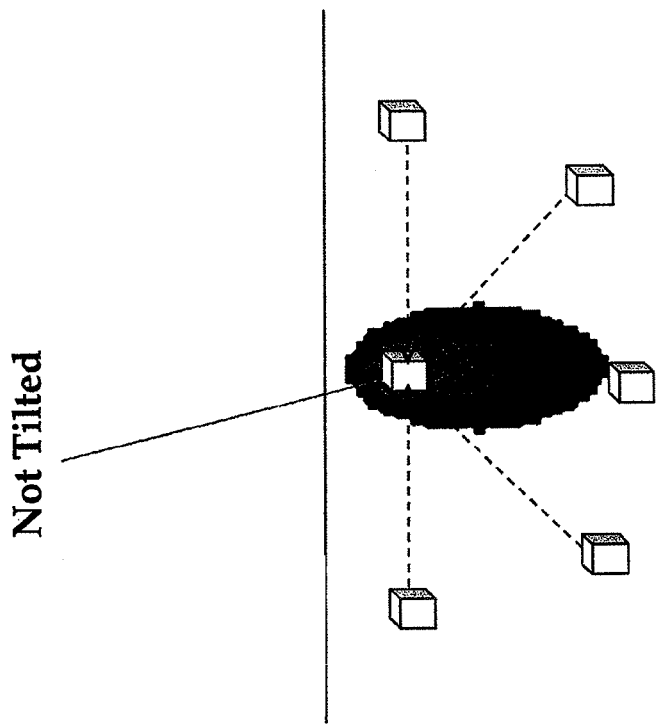
FIG. 7A Tilted
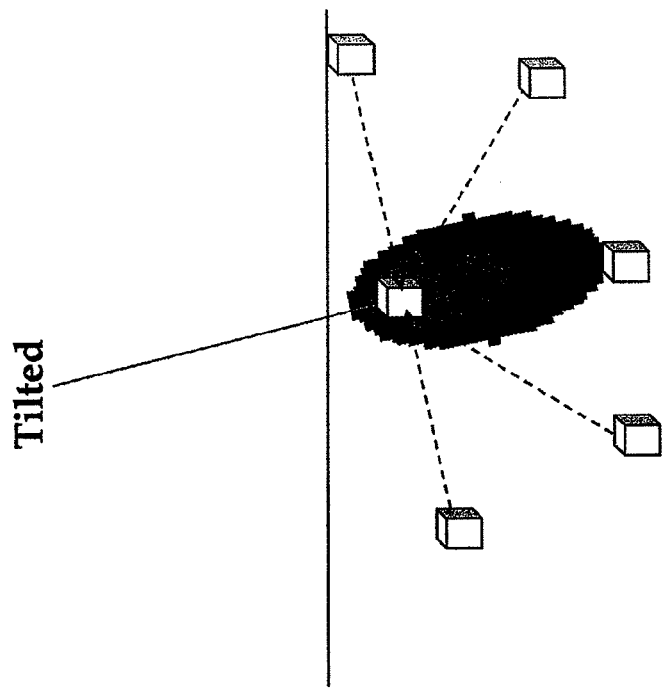
FIG. 7B Not Tilted

DOSE COMPUTATION FOR RADIATION THERAPY USING HETEROGENEITY COMPENSATED SUPERPOSITION

CROSS-REFERENCE OF RELATED APPLICATION

This is a national stage application under 35 U.S.C. §371 of PCT/US2012/058345 filed Oct. 1, 2012, the entire contents of which are incorporated herein by reference and this application claims priority to U.S. Provisional Application No. 61/540,773 filed Sep. 29, 2011, the entire contents of which are hereby incorporated by reference.

BACKGROUND

1. Field of Invention

The current invention relates to radiation therapy systems, and more particularly radiation therapy systems that irradiate non-homogeneous distributions of matter.

2. Discussion of Related Art

Radiation therapy is the medical use of radiation to treat malignant cells, such as cancer cells. This radiation can have an electromagnetic form, such as a high-energy photon, or a particulate form, such as an electron, proton, neutron, or alpha particle.

By far, the most common form of radiation used in practice today is high-energy photons. Photon absorption in human tissue is determined by the energy of the radiation, as well as the atomic structure of the tissue in question. The basic unit of energy used in radiation oncology is the electron volt (eV); $10^3$ eV=1 keV, $10^6$ eV=1 MeV. At therapeutic energies the three major interactions between photons and tissue are: the photoelectric effect, Compton effect, and pair production.

In the photoelectric effect, an incoming photon transfers energy to a tightly bound electron. The photon transfers practically all of its energy to the electron and ceases to exist. The electron departs with most of the energy from the photon and begins to ionize surrounding molecules. This interaction depends on the energy of the incoming photon, as well as the atomic number of the tissue; the lower the energy and the higher the atomic number, the more likely that a photoelectric effect will take place. The energy range in which the photoelectric effect predominates in tissue is about 10-25 keV.

The Compton effect is the most important photon-tissue interaction for the treatment of cancer. In this case, a photon collides with a "free electron," i.e., one that is not tightly bound to the atom. Unlike the photoelectric effect, in the Compton interaction both the photon and electron are scattered. The photon can then continue to undergo additional interactions, albeit with a lower energy. The electron begins to ionize with the energy given to it by the photon. The probability of a Compton interaction is inversely proportional to the energy of the incoming photon and is independent of the atomic number of the material. The Compton effect dominates in the range of ~25 keV-25 MeV and is therefore the most common interaction occurring clinically, as most radiation treatments are performed at energies of about 6-20 MeV.

In pair production, a photon interacts with the nucleus of an atom. The photon gives up energy to the nucleus and, in the process, creates a positron-electron pair of particles. The positive electron (positron) ionizes until it combines with a free electron in positron-electron annihilation. This positron-electron annihilation generates two photons that travel in opposite directions. The probability of pair production is proportional to the logarithm of the energy of the incoming photon and is dependent on the atomic number of the material. The energy range in which pair production dominates is ≥25 MeV. This interaction occurs to some extent in routine radiation treatment with high-energy photon beams.

With the advent of high-energy linear accelerators, electrons have become a viable option in treating superficial tumors up to a depth of about 5 cm. Electron depth dose characteristics are unique in that they produce a high skin dose but exhibit a falloff after only a few centimeters.

Electron absorption in human tissue is greatly influenced by the presence of air cavities and bone. The most common clinical uses of electron beams include the treatment of skin lesions, such as basal cell carcinomas, and boosting of areas that have previously received photon irradiation, such as postoperative lumpectomy or mastectomy scar in breast cancer patients, as well as select nodal areas in the head and neck.

Fast, accurate dose computation algorithms are important for radiation therapy planning as they are the only available method of ensuring that the desired dose is delivered to a specific patient. Dose computation includes two parts: a source model and a transport model. The source model provides the incident fluence. The transport model computes the dose that results from the incident fluence and is currently the performance bottleneck. The three main transport algorithms in the order of increasing accuracy/decreasing performance are pencil beam, superposition/convolution, and Monte Carlo. Superposition/convolution is the current clinical standard method of calculating radiation dose for external beam radiation therapy.

In recent years, treatment quality has been increased by the use of intensity modulation. This technique uses a multi-leaf collimator to define multiple apertures from a single beam direction providing the ability to vary the intensity of radiation across the beam. This technique allows us to conform radiation treatment to the shape of the target and avoid critical structures while drastically increasing the number of beam parameters. In order to determine the best set of multi-leaf collimator settings, the treatment planning system must optimize, through multiple iterations of dose calculations, an objective function having the drastically increased number of beam parameters. In practice, the treatment planner repeats the optimizations multiple times in order to achieve the best results possible for the patient. Therefore, while a single optimization may take five minutes for a set of five beams, the entire process may take several hours to produce a clinically acceptable plan. This limits both the quantity and quality of intensity modulated plans in clinical work flow.

This clinical workflow limitation extends to more complex techniques such as volumetric modulated arc therapy (Otto, K., Med. Phys. 35, 310-317, 2008), intensity modulated arc therapy (Yu, C. X., Phys. Med. Biol. 40, 1435-1449, 1995), and adaptive radiation therapy (Yan, D., Vicini, F., Wong, J., Martinez, A, Phys. Med. Biol. 42, 123-132, 1997). Furthermore, this clinical workflow limitation prohibits real-time radiation therapy; the ability to scan, re-plan and treat every patient daily. A thorough review of dose calculation in radiation therapy is available from Ahnesjo et al. (Ahnesjo, A., Aspradakis, M, Phys. Med. Biol. 44, R99-R155 1999).

Thus, computational performance of the dose computation is a limiting factor in radiation therapy treatment plan quality. Traditionally, improvements in treatment quality have been realized by faster hardware. But, Moore's law has changed. Instead of doubling in speed every 18 months, computers are doubling the number of processing cores. And as processors are becoming multi-core, the many-core architectures of graphics processing units (GPUs) are gaining the flexibility to run general purpose algorithms. To realize the promised performance gains from the recent trend in computer hardware, the serial algorithms used in radiation dose computation should be replaced with parallel ones. Recently, the Nucletron corporation has made an announcement regarding GPU acceleration in their treatment planning system, though published details are not yet available. Straight-forward partitioning of the existing serial algorithms to produce multiple threads for multiple processing cores does not work. This is because the threads are farmed out to calculate the same radiation dose based on the same input data and read/write conflicts may easily arise. For example, when a write-on-write (WOW) conflict arises only the last write is stored, leading to inaccurate dose calculations. In addition, conventional methods of performing real-time radiation treatment planning do not provide good results for discontinuities in irradiated matter. Therefore, there remains a need for improved radiation dose planning methods and systems for taking into account heterogeneous density distributions with irradiated bodies.

SUMMARY

A system for radiation therapy according to some embodiments of the current invention includes a radiation planning system. The radiation planning system includes a data processor that is adapted to receive information concerning an intended radiation treatment region of a body, receive a calculated initial energy released per unit mass for a plurality of locations within the body, compute a radiation dose at a plurality of locations within the radiation treatment region based on the calculated initial energy released per unit mass and including radiation dose contributions due to scattering from other locations within the body, and determine radiation therapy parameters for providing radiation treatment to the intended radiation treatment region based on the radiation dose computed at the plurality of locations within the radiation treatment region. Including radiation dose contributions due to scattering from other locations within the body take into account density discontinuities in the body.

A method for determining radiation therapy parameters for radiation treatment according to some embodiments of the current invention includes receiving information concerning an intended radiation treatment region of a body, receiving a calculated initial energy released per unit mass for a plurality of locations within the body, computing a radiation dose at a plurality of locations within the radiation treatment region based on the calculated initial energy released per unit mass and including radiation dose contributions due to scattering from other locations within the body, and determining the radiation therapy parameters for providing the radiation treatment to the intended radiation treatment region based on the radiation dose computed at the plurality of locations within the radiation treatment region. The including radiation dose contributions due to scattering from other locations within the body take into account density variations in the body.

A computer readable medium according to some embodiments of the current invention contains non-transitory executable code. The non-transitory executable code, when executed by a computer, causes the computer to receive information concerning an intended radiation treatment region of a body, receive a calculated initial energy released per unit mass for a plurality of locations within the body, compute a radiation dose at a plurality of locations within the radiation treatment region based on the calculated initial energy released per unit mass and including radiation dose contributions due to scattering from other locations within the body, and determine radiation therapy parameters for providing radiation treatment to the intended radiation treatment region based on the radiation dose computed at the plurality of locations within the radiation treatment region. Including radiation dose contributions due to scattering from other locations within the body take into account density discontinuities in the body.

BRIEF DESCRIPTION OF THE DRAWINGS

Further objectives and advantages will become apparent from a consideration of the description, drawings, and examples.

FIGS. 7A and 7B illustrate titled kernel and non-tilted kernel during the superposition operation.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
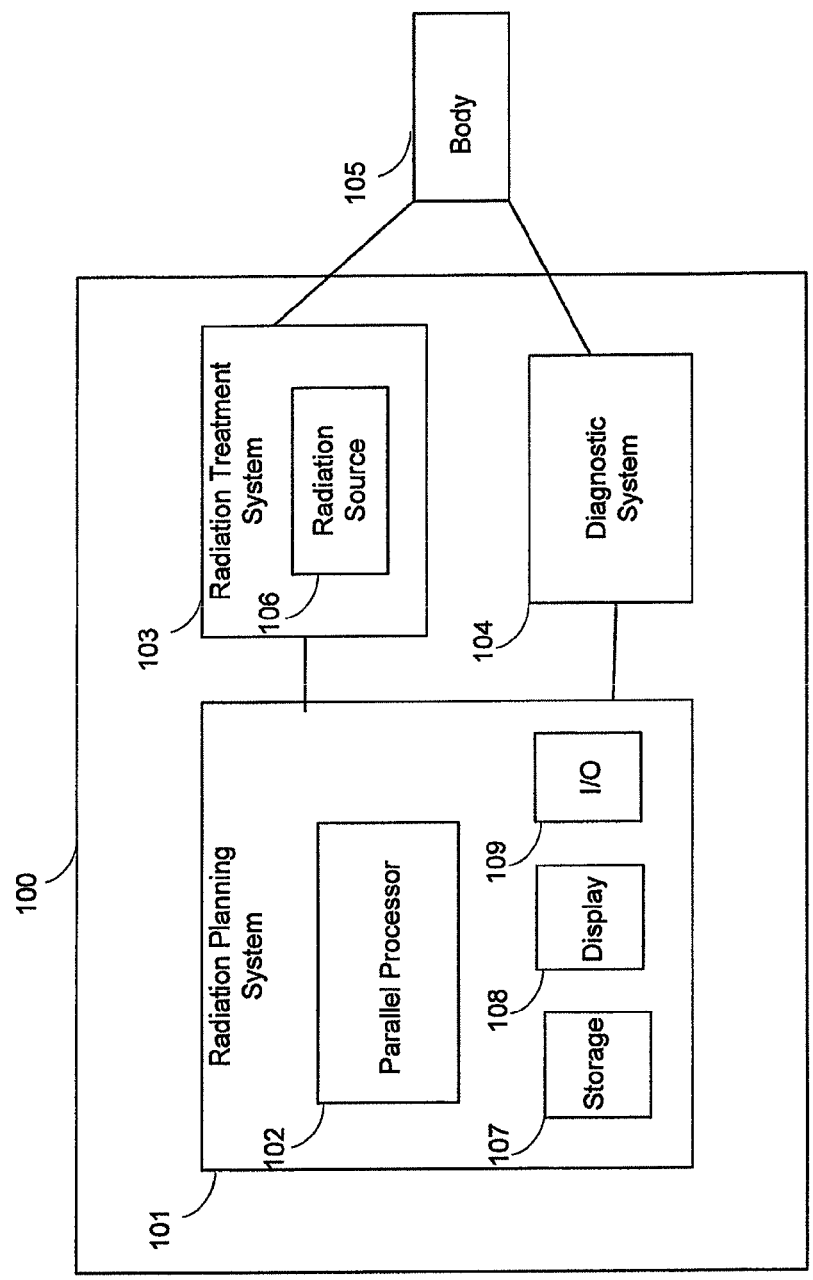
FIG. 1 shows a schematic diagram of an embodiment of the present invention.

FIG. 1 is a schematic diagram of a radiation therapy system 100 according to an embodiment of the current invention. Radiation therapy system 100 comprises a radiation planning system 101, which further comprises a data processor 102. Data processor 102 can be a single processor, a multi-processor, a distributed processor that is distributed over a network, and/or a parallel processor, such as, but not limited to, one or more graphics processing units (GPUs). Data processor 102 is adapted to receive input information concerning a body 105 having an intended radiation treatment region. Data processor 102 is also adapted to generate output information for providing radiation treatment to the intended radiation treatment region of the body 105. Data processor 102 can be adapted to perform a plurality of reverse ray tracing calculations based on the received input information in determining the output information for providing radiation treatment. Each reverse ray tracing comprises calculating a first physical property corresponding to a first sub-region of the intended radiation treatment region of the body that is intersected by a ray traced from a source position through the intended radiation treatment region; and calculating, subsequent to the first-mentioned calculating, a second physical property corresponding to a second sub-region of the intended radiation treatment region that is intersected by the ray at a location closer to the source position than is the first sub-region. The radiation planning system 101 may further comprise storage 107, display 108, and I/O 109. Storage 107 may be, for example, a hard disk drive, a CD-ROM drive, a DVD drive, a flash drive, etc. Display 108 may be, for example, a Liquid Crystal Display (LCD), a cathode ray tube (CRT) monitor, a plasma display, etc. I/O device 109 may include, for example, a mouse, a keyboard, an interface for data transfer over a network or a data bus, etc.

Radiation therapy system 100 may further comprise a radiation treatment system 103 that is in communication with radiation planning system 101. Radiation treatment system 103 further comprises a radiation source 106. Radiation source 106 is a source that emits a beam of radiation to be directed onto body 105 for treatment. Examples of radiation sources may include an X-ray source, a gamma ray source, an electron beam source, etc. Radiation source 106 may further comprise a multi-leaf collimator (MLC) to collimate the beam. By adjusting the position of the leaves of the MLC, a dosimetrist may match the radiation field to a shape of the treatment region of body 105. Other beam shaping and/or contouring can be included in some embodiments. Radiation source 106 can have a corresponding source model. Radiation system 103 may be controlled by radiation treatment planning system 101, for example, to deliver intensity modulated radiation energy to conform radiation treatment to the shape of the intended radiation treatment region of the body 105.

Radiation therapy system 100 may further comprise a diagnostic system, in communication with the radiation planning system 101, that generates empirical data of body 105. The empirical data may be used as input information to radiation planning system 101 and data processor 102 and may be used in reverse ray tracing calculations. Diagnostic system 104 comprises sensors to obtain the empirical data of body 105. An example diagnostic system may be a Computed Tomography (CT) scanner, a Magnetic Resonance Imaging (MRI) scanner, a Positron Emission Tomography (PET) scanner, etc. Body 105 can be a human or an animal, for example.

A system for radiation therapy 100 according to an embodiment of the current invention includes a radiation planning system, which in turn includes data processor 102 adapted to receive information concerning an intended radiation treatment region of a body, receive a calculated initial energy released per unit mass for a plurality of locations within the body, compute a radiation dose at a plurality of locations within the radiation treatment region based on the calculated initial energy released per unit mass and that also includes radiation dose contributions due to scattering from other locations within the body, and determine radiation therapy parameters for providing radiation treatment to the intended radiation treatment region based on the radiation dose computed at the plurality of locations within the radiation treatment region. Including radiation dose contributions due to scattering from other locations within the body takes into account density discontinuities in the body. The density discontinuities in the body that are taken into account in the computing can include interfaces between different types of matter within the body. The interfaces between different types of matter within the body can include an interface between at least two of bone, tissue, an internal organ, air, water and an artificial implant, for example. However, any interfaces between matter of different densities are intended to be included within the general concepts of the current invention.

In some embodiments, the computation of the radiation dose at each of the plurality of locations within the radiation treatment region can include an integration of the initial energy released per unit mass over the plurality of locations within the body weighted by a kernel function. This can be a convolution integration, for example. In some embodiments, the kernel function can include an empirically determined effective density function to take into account the density variations in the body.

In some embodiments, the integration can be for a first radiation beam energy and In some embodiments, the computing the radiation dose at each of the plurality of locations within the radiation treatment region can further include a second integration of the initial energy released per unit mass over the plurality of locations within the body weighted by a kernel function for a second radiation beam energy, and the computing the radiation dose at each of the plurality of locations within the radiation treatment region further comprises adding the first and second integrations. This can be extended to more than two energies in some embodiments. For example, four or more integrations at four or more different energies could be performed in some embodiments of the current invention.

In some embodiments, the system for radiation therapy can further include, prior to the receiving the calculated initial energy released per unit mass for a plurality of locations within the body, calculating the initial energy released per unit mass. This calculation can be, but is not limited to a TERMA calculation, such as described in more detail below. However, in other embodiments it can be, or can include, a kinetic energy released per unit mass (KERMA) and/or scatter energy released per unit mass (SCERMA) calculation. In some embodiments, the calculating the initial energy released per unit mass can include a back-projected ray tracing calculation.

In some embodiments, the determining the radiation therapy parameters for providing radiation treatment to the intended radiation treatment region can be sufficiently fast to be performed in real-time during a radiation treatment procedure.

The superposition/convolution algorithm has been shown to produce an accurate calculation of the dose distribution (Mackie, T. R., Scrimger, J. W., Battista, J. J., Med. Phys. 12, 188-196, 1985; Mackie, T. R., Ahnesjo, A., Dickof, P., Snider, A, Use of Comp. In Rad. Ther., 107-110 1987; Mackie, T. R., Reckwerdt, P. J., McNutt, T. R., Gehring, M., Sanders, C., Proceedings of the 1996 AAPM Summer School, 1996). It includes two stages. First, the incident fluence is transported through the density representation of the patient to compute the Total Energy Released per unit MAss (TERMA) at each location. The TERMA, $T_E(r')$, of a particular energy E of at point r' is defined as the fluence of energy E, $\Psi_E(r')$, weighted by the mass density relative to water, $\rho_{md}(r')$, and linear attenuation, $\mu_E(r')$, at point r', as shown in the following Eq. 1.

$$T_E(r') = \frac{\mu_E(r')}{\rho_{md}(r')} \Psi_E(r'). \tag{1}$$

The linear attenuation coefficient, $\mu_E(r')$, is also dependent on the atomic material. Since Compton scattering dominates in the energy range of mega volts associated with radiation therapy and Compton scattering is dependent on electron density not material, clinically, there is a piecewise linear relation between standard CT numbers and density for normal human tissues. In general, non-Compton interactions are considered negligible in this energy range. The fluence, $\Psi_E(r')$, at point r' of energy E is determined by the source focal point s and the incident fluence $\Psi_{E,0}(r')$ of energy E in the direction r' according the following Eq. 2:

$$\Psi_E(r') = \frac{\Psi_{E,0}(r')}{\|r'-s\|^2} e^{\int_s^{r'} -\mu_E(t)dt}. \tag{2}$$

Then, the superposition/convolution algorithm spreads this energy by a dose deposition kernel to determine the final dose at each location. To allow the dose deposition kernel to scale realistically with tissue inhomogeneities the radiological (a.k.a. the electron density, $\rho_{ed}$ weighted) distance between points, $d_\rho(r,r')$, is used, based on the following Eq. 3, which differentiates superposition from convolution.

$$d_\rho(r,r') = \int_r^{r'} \rho_{ed}(t)dt \tag{3}$$

The dose at point r, D(r), is computed from an integration over the TERMA volume weighted by the energy dependent dose deposition kernel, $K_E$, according to the following Eq. 4. The standard collapsed cone kernel is indexed by radiological distance and relative angle, $\omega$, between the point and the kernel axis, and lacks the geometric distance squared effect.

$$D(r) = \int\int\int \sum_E T_E(r') K_E(d_\rho(r,r'), \omega(r,r')) \frac{1}{\|r-r'\|^2} dr'. \tag{3}$$

Typically the mono-energetic contribution of every voxel, as in Eq. 4, is not calculated. Instead, as in Eq. 7, which is based on Eqs. 5 and 6, a discrete set of ray angles, $\omega$, and directions, v, are chosen and integrated along using a single poly-energetic kernel. This is justified by the approximately exponential kernel fall-off and the drastically reduced contribution of any single distant voxel due to the distance squared effect. The distance squared effect is negated by the increase in volume of the solid angle the rays represent. Ray directions are chosen to balance geometric and kernel energy factors.

$$T(r') = \sum_E \frac{\Psi_E}{\sum_E \Psi_E} T_E(r'). \tag{5}$$

$$K(d_r, \omega) = \sum_E \frac{\Psi_E}{\sum_E \Psi_E} K_E(d_r, \omega). \tag{6}$$

$$D(r) \approx \sum_{\omega,v} \int T(r+tv) K(d_\rho(r, r+tv), \omega) dt. \tag{7}$$

Traditionally, TERMA is calculated by casting a set of rays that deposit the incident fluence to volume according to Eqs. 1 and 2. For numerical accuracy, approximately four rays should pass through each TERMA voxel, attenuation should begin at the patient's surface and the fluence to each voxel should be normalized by the total length of the rays that contributed to that voxel. This normalization removes the normal inverse square fluence drop-off due to a diverging source. The normalization must therefore be reapplied, normally to the TERMA grid. A clinically acceptable speed enhancement is to not tilt the dose deposition kernel to align with the ray axis at each voxel. In this case it is more accurate to apply the divergence correction to the dose grid (Papanikolaou, N., Mackie, T. R., Meger-Wells, C., Gehring, M., Reckwerdt, P., Med. Phys. 20, 1327-1336, 1993).

TERMA is strongly dependent on the beam spectrum. The spectrum is rotationally symmetric about the beam axis and hardens with depth in material. By a hardened spectrum, we mean that the spectrum becomes more dominated by higher energy components as lower energy components are more preferentially scattered and absorbed out of the beam. Traditionally, the attenuation is modeled using a lookup table which when combined with the linear attenuation lookup table has axes of depth, density and off-axis angle. This table also requires the use of a fixed step ray-casting algorithm, which avoids evaluating the traditionally costly exponential at every step. Though clinically accepted for performance reasons, this look-up table assumes a homogenous medium. This is incorrect as heterogeneous tissues preferentially attenuate different spectra. Furthermore, the fixed step size and discretized rays results in numerical artifacts.

The dose deposition kernel also has a dependence on the energy spectrum at each voxel. However, a single poly-energetic kernel has been shown to be sufficiently accurate for clinical use when used with a non-physical beam spectrum and is the current standard of care. Poly-energetic kernels are created by combining a spectrum of mono-energetic kernels, which are generated using Monte Carlo simulations that forces mono-energetic photons to interact at the center of a water sphere and tallying the dose deposited everywhere in that sphere (Ahnesjo, A., Andreo, P., Brahme, A., Acta. Oncol., 26, 49-56, 1987; Mackie, T. R., Bielajew, A. F., Rogers, D. W. O., Battista, J. J., Phys. Med. Biol. 33, 1-20,1988).

Algorithms for image processing have obviously been adapted to parallel or graphic processing unit (GPU) architectures. There are several ray cast, ray trace and volumetric visualization algorithms adapted in conventional graphics systems, for example. However, dose calculation for radiation therapy is fundamentally concerned with the interaction of a line with a volume while visualization algorithms are interested in a property of a line, such as its integral or maximum. This distinction renders many parallel ray tracing algorithms developed for visualization inapplicable for radiation therapy. Part of the traditional TERMA algorithm may be superficially similar to volumetric ray-casting although naïvely adapting the previous GPU implementation as done in (Krüger, J., Westermann, R., 2003) is impractical and would fail to produce accurate results. Because dose deposition deals primarily with electron interactions, it is fundamentally different from visualization algorithms.

According to an embodiment of the current invention, the superposition/convolution algorithm can be adapted to the GPU using a combination of NVIDA's Compute Unified Device Architecture (CUDA) software development environment and the Digital Mars' D programming language. The following describes the details of the adaptation.

As discussed, superposition/convolution is a two stage algorithm: first the TERMA is calculated and then the dose deposition kernel is superimposed.

During the TERMA calculation, a standard forward TERMA algorithm may be implemented. This method requires overlapping scattered accumulation, which results in read-write conflicts when run in parallel. A read-write conflict occurs when threads simultaneously attempt to read, process and then write to the same memory, resulting in only the last update being recorded. This drastically reduces the effective number of contributing rays to each voxel to below the limit required for numerical accuracy. However, the divergent nature of the source may be utilized to create sets of rays guaranteed to be one voxel apart at all times. While individual sets are large enough to be efficiently run on the GPU, this serialization causes excessive GPU call overhead. The traditional 3D spectral attenuation lookup table exceeded the texture cache size, reducing performance. Performance can be improved by individually attenuating separate spectral bins, using shared memory to reduce register usage. This reduced the lookup to a small 2D texture of linear attenuation coefficients parameterized by energy and density. This may be enabled by the hardware accelerated exponential on the GPU. Accuracy can also be improved as the spectrum is correctly attenuated in heterogeneous media. However, the number of rays required for numerical accuracy exhibited an unclear relation with resolution, discretization effects can be evident, as will be discussed, and computation may comprise a significant fraction of the total dose calculation time.

These issues can be avoided by a back-projected TERMA algorithm according to some embodiments of the current invention. By rearranging equations (1), (2) and (5), separating the incidence fluence, $\Psi_{E,0}(r')$, into a spectral weight, $W_E$, and net fluence factor, $\Psi_0(r')$, and defining an attenuation factor, the following Eq. 8 is obtained.

$$A(r') = \frac{1}{\|r' - s\|^2} \sum_E w_E(r') \frac{\mu_E}{\rho_{md}(r')} e^{\int_s^{r'} -\mu_E(t)dt} \quad (8)$$

Figure 2:
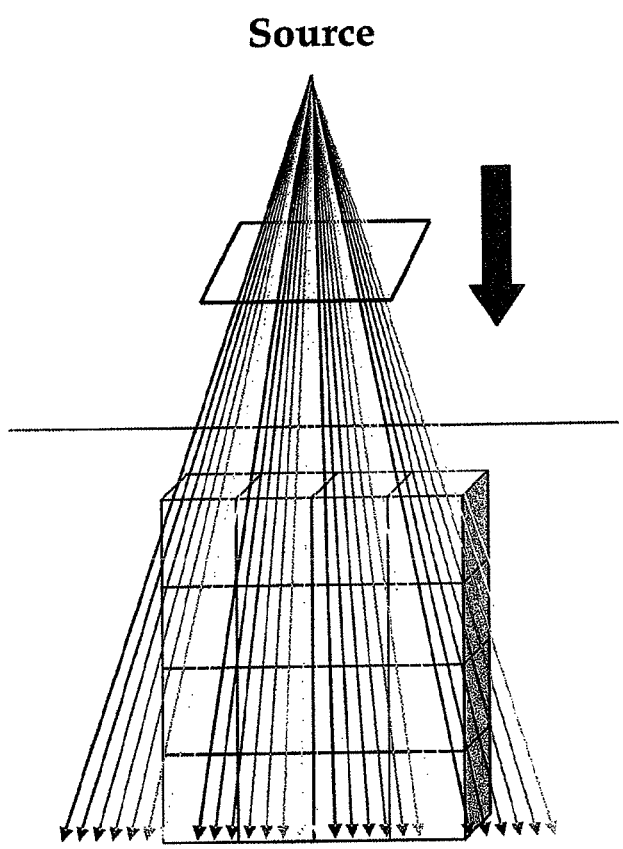
FIG. 2 illustrate a conventional forward ray tracing.
Figure 3:
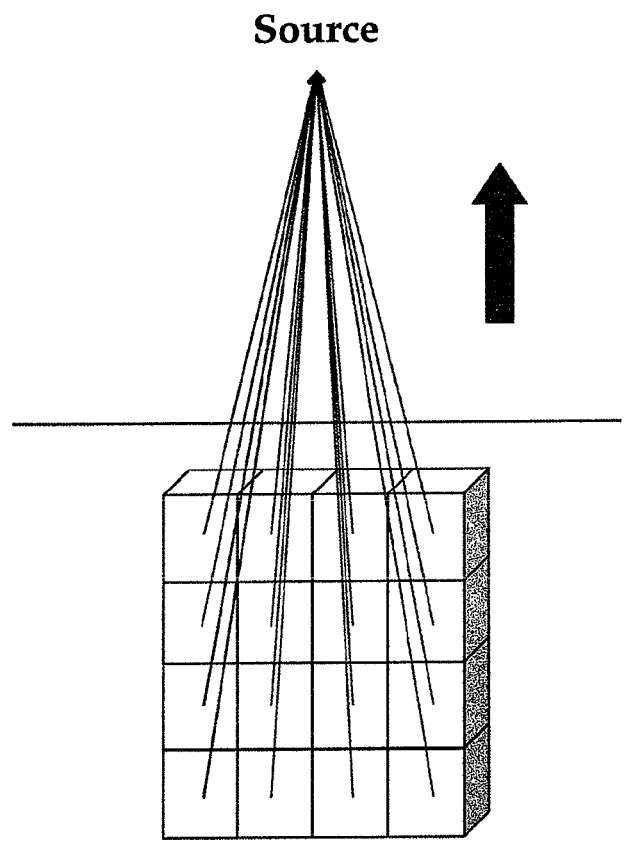
FIG. 3 illustrates a back-projected ray tracing according to an embodiment of the present invention.

FIG. 2 illustrates a conventional forward ray tracing. FIG. 3 illustrates a back-projected ray tracing according to an embodiment of the present invention. By casting a ray from each TERMA voxel back towards the source, gathering the net attenuation along the way, early ray termination can be achieved when the patient boundary is reached, increasing both performance and accuracy. In calculating the above defined attenuation factor, a pre-compiled look-up table may be used for the quantity $$\frac{\mu_E}{\rho_{md}}.$$

For example, based on a CT image, in Hounsfield units, of a radiation treatment region, one may look up this quantity from the look-up table. The spectral weight, $W_E$, for example, may be contained in a model of the radiation source for the radiation treatment, and each spectral bin may be attenuated independently for a given ray.

Then TERMA may then be calculated by multiplying the net attenuation for each voxel by the net incident fluence from the source towards that voxel according to the following Eq. 9:

$$T(r') = \Psi_0(r')A(r'). \quad (9)$$

Figure 4:
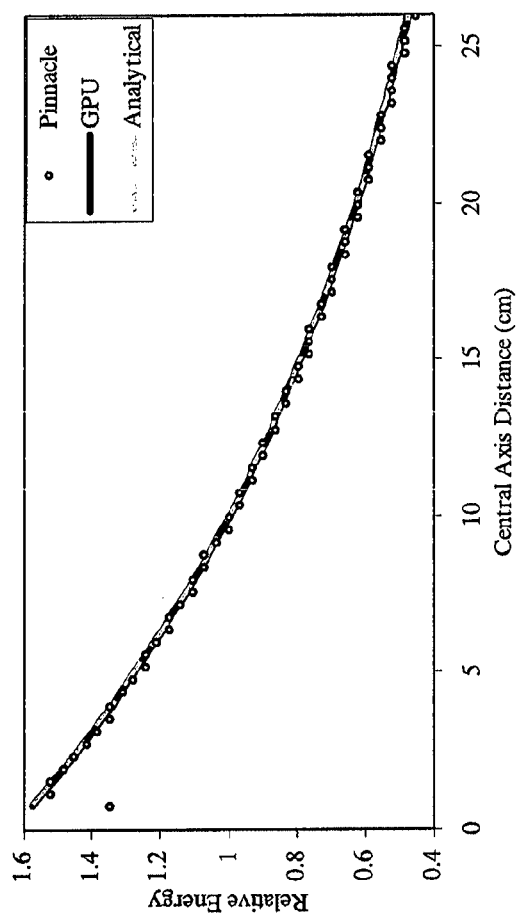
FIG. 4 shows the Total Energy Released per unit Mass (TERMA) along the central axis calculated analytically, using a commercial Pinnacle system (Philips Radiation Oncology Systems Madison Wis.) and an embodiment of the present invention, each normalized at a depth of 10 cm.

FIG. 4 shows TERMA energies along the central axis calculated analytically, using the commercial Pinnacle[3] system (Philips Radiation Oncology Systems Madison Wis.), and according to an embodiment of the present invention, each normalized at a depth of 10 cm.

While Eq. 9 is an $O(n^4)$ algorithm, as opposed to the $O(n^{-3})$ for the standard forward method, each thread only writes to its own voxel, thus avoiding read-write conflicts. The algorithm allows for coalesced read access to texture memory which drastically enhances memory performance. Both the standard forward and the back-projected ray-tracing algorithms may be used over a variety of clinical resolutions and may compute the computationally expensive attenuation volume once during interactive use or intensity modulation optimization, when only the fluence field is changed. This pre-computation can provide a multiple order of magnitude performance improvement according to some embodiments of the current invention.

TABLE 1

Performance of the standard forward, back-projected and approximate TERMA calculation methods. Also included is the performance of only updating the incidence fluence field which is useful during intensity modulation.

| Size | Forward | Back-projected | Approximate attenuation | Intensity Modulation |
|------|---------|----------------|-------------------------|----------------------|
| $32^3$ | 23 ms | 2 ms | 1 ms | 1 ms |
| $64^3$ | 44 ms | 18 ms | 2 ms | 1 ms |
| $128^3$ | 150 ms | 220 ms | 26 ms | 3 ms |
| $256^3$ | 1869 ms | 3317 ms | 454 ms | 13 ms |

Performance of the attenuation volume based TERMA algorithm relative to the traditional ray cast algorithm was compared across a variety of resolutions as shown in Table 1. Both methods incorporate physically correct multi-spectral attenuation and have been optimized for the GPU. Ray-cast, used in forward ray tracing calculations, can have read/write conflicts. The scalability of ray-cast exhibits sweet spots and required parameter tweaking to maintain the prerequisite number of rays traversing each voxel. The tweaking is laborious and highly unintuitive. The attenuation volume based TERMA computation by back-projected ray tracing calculations exhibits an empirical performance of $O(n^{3.76})$, which is a slight improvement over its theoretical $O(n^4)$. Back-projected ray tracing calculations, according to some embodiments of the current invention, does not suffer from read/write conflict. The fast, approximate radiological depth based attenuation algorithm, which makes the standard homogeneous material approximation, provided a speedup of ~8×. The performance of only updating the incident fluence, as commonly used in intensity modulation in treatment planning, is reported under intensity modulation.

Figure 5A:
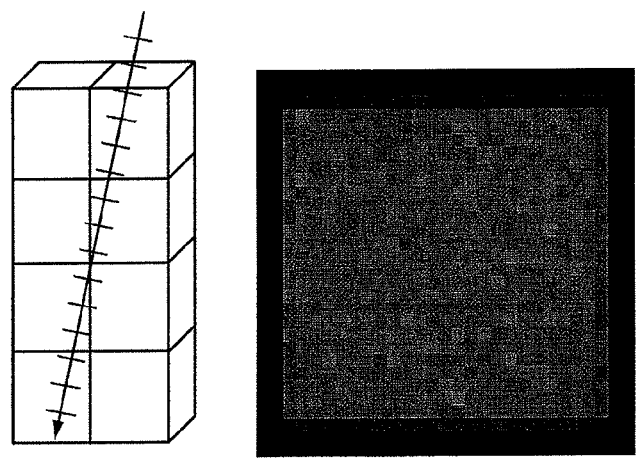
FIG. 5A shows a penumbra slice of TERMA with discretization artifacts calculated using forward tracing.
Figure 5B:
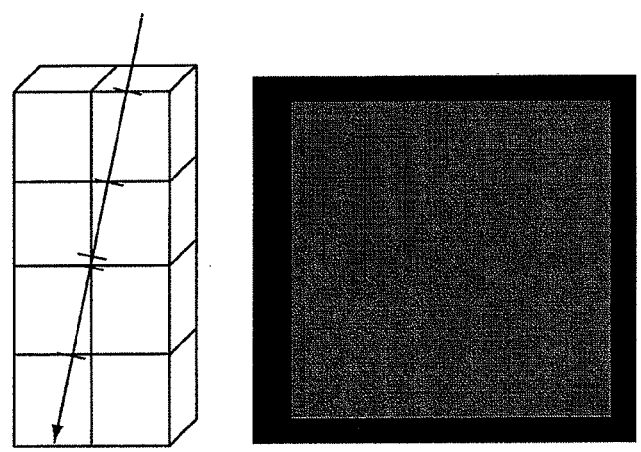
FIG. 5B shows the same penumbra slice of TERMA without discretization artifacts calculated using an embodiment of the present invention.

One advantage of the back-projected ray tracing calculation is the elimination of artifacts due to ray discretization. This is because an exact radiological path can be used in the back-projected ray-tracing method, similar to the rasterization method (Amanatides, J., Woo., A., Eurographics'87, Conference Proceedings, 1987), which reduces the per ray per voxel memory accesses to one and eliminates related discretization artifacts. FIGS. 5A and 5B show calculated slices of TERMA using a fixed step size and an exact radiological distance according to an embodiment of the present invention, respectively.

Figure 6A:
FIGS. 6A and 6B show calculated slices of TERMA using a fixed step size and an exact radiological distance step size according to an embodiment of the present invention, respectively.
Figure 6B:
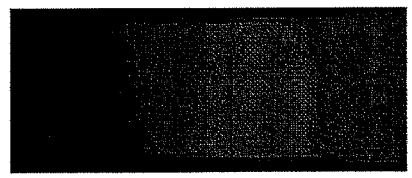

Further, physically correct multi-spectral attenuation (Liu, H. H., Mackie, T. R., McCullough, E. C., Med. Phys. 24, 1729-1741, 1997) can be applied in the back-projected ray tracing calculations. For interactive beam angle changes, a simpler variant without physically correct multi-spectral attenuation can be implemented, as typically used in current clinical systems and can result in a significant performance improvement. During the TERMA calculation, physically correct multi-spectral attenuation (Liu, H. H., Mackie, T. R., McCullough, E. C., Med. Phys. 24, 1729-1741, 1997) can be used for the back-projected ray calculations. The current clinical standard is a fixed-step, fast, approximate forward method which lacks physically correct multi-spectral attenuation. The use of a cached attenuation volume, as identified according to some embodiments of the current invention, can be used to accelerate the TERMA calculation. FIG. 6A shows a penumbra slice of TERMA with discretization artifacts calculated using the standard forward ray tracing without multi-spectral attenuation. FIG. 6B shows the same penumbra slice of TERMA without discretization artifacts calculated according to an embodiment of the present invention with multi-spectral attenuation.

Once TERMA is calculated, superposition of a dose deposition kernel can be used to compute the amount of absorbed radiation energy. Superposition has two standard formulations. The forward formulation spreads dose from a TERMA voxel to the surrounding dose voxels. This forward formulation requires calculating the dose to every patient voxel and suffers from read-write conflicts as multiple TERMA voxels contribute to every dose voxel. The inverse kernel formulation gathers the contribution to a dose voxel from the surrounding TERMA voxels. This is computationally efficient as only the dose to the volume of interest is calculated. This is possible because the dose deposition kernel is invertible.

FIGS. 7A and 7B illustrate the titled kernel and the non-tilted kernel during the superposition operation. Strictly speaking, use of kernel tilting in standard superposition breaks the invertible kernel assumption. However, given the distant source and the kernel's rapid fall-off, invertibility is still a reasonable assumption and is in clinical use. Nonetheless, the kernel's rapid fall-off also creates numerical sampling issues at typical clinical resolutions. There are two standard alternatives. The cumulative kernel (CK) (Ahnesjo, A., Med. Phys. 16, 577-92, 1989) represents the dose deposition from a ray segment to a point, according to the following Eq. 10.

$$CK(x,\omega)=\int_0^x K(t,\omega)dt. \quad (10)$$

The cumulative-cumulative kernel (CCK) (Lu, W., Olivera, G. H., Chen, M., Reckwerdt, P. J., Mackie, T. R., Phys. Med. Biol. 50, 655-680, 2005) represents the dose deposition from a ray segment to a ray segment.

$$CCK(x,\omega)=\int_0^x CK(t,\omega)dt. \quad (11)$$

Both are derived from integrating the standard point to point kernel, $K(d_r,\omega)$, for particular radiological depths, $d_r$, and angles, $\omega$.

$$\int_x^{x+\Delta x} K(v,\omega)dv=CK(x+\Delta x,\omega)-CK(x,\omega). \quad (12)$$

$$\int_0^{\Delta s} CK(x+u,\omega)du=CCK(x+\Delta s,\omega)-CCK(x,\omega). \quad (13)$$

$$\int_0^{\Delta s}\int_{x+v}^{x+\Delta x+v} K(u,\omega)dudv=(CCK(x+\Delta s+\Delta x,\omega)-CCK(x+\Delta x,\omega))-(CCK(x+\Delta s,\omega)-CCK(x,\omega)). \quad (14)$$

While more accurate, particularly at coarser resolutions, the CCK formulation has traditionally been 50% slower than the CK formulation. However, the GPU's texture unit, which caches memory accesses and provides dedicated linear interpolation hardware, allows the use of the CCK formulation with a negligible performance decrease. Thus, the superposition calculation can be enhanced with the cumulative-cumulative kernel (Lu, W., Olivera, G. H., Chen, M., Reckwerdt, P. J., Mackie, T. R., Phys. Med. Biol. 50, 655-680, 2005).

Serial CPU implementations allow the reuse of ray-cast index calculation, by moving all indexes one voxel over. But, this prevents kernel tilting, resulting in errors at large off-axis angles, as will be discussed in Table 2. In contrast, some embodiments of the present invention implemented on a GPU allow both tilting and non-tilting kernels to be calculated. Kernel tilting has traditionally resulted in 300% loss in performance (Liu, H. H., Mackie, T. R., McCullough, E. C., Med. Phys. 24, 1729-1741, 1997), but some embodiments of the present invention implemented on a GPU have a performance loss of only 19%.

Because the superposition operation maintains accuracy at coarse resolutions and the kernel exhibits rapid fall-off at edges, a multi-resolution superposition algorithm that approximates each ray as a true solid angle can be employed according to some embodiments of the current invention. Unlike a ray, the width of a solid angle increases with geometric distance. In a discretized volume, a ray's width is proportional to the voxel's width. Therefore, by increasing the voxel width with geometric distance, a ray can approximate a solid angle. This approximation also increases the step size in a logarithmic manner which increases the performance by shrinking the computational complexity from $O(\omega DT^{1/3})$ to $O(\omega D\log(T^{1/3}))$; where $\omega$ is the number of angles, D is the number of dose voxels, and T is the number of TERMA voxels.

Compared to the standard method, the multi-resolution superposition according to an embodiment of the present invention exhibits an interesting accuracy trade-off. Table 2 compares the accuracy of the multi-resolution superposition algorithm according to some embodiments of the present invention to the standard methods across multiple field sizes and kernel ray samplings. The multi-resolution superposition algorithm according to some embodiments of the present invention generally can perform better in the penumbra and low dose regions for small field sizes, as less TERMA is geometrically missed by rays. However, accuracy in the high dose region may be compromised slightly as the larger steps can cause the beam boundary to be blurred. A variant of the multi-resolution superposition algorithm as a variant embodiment of the present invention, using the same step sizes, but not using a multi-resolution data structure can exhibit reduced cache performance and may increase the mean error by 60% on average.

block represents one parallel work unit and therefore is limited in size. Block thread counts were optimized using NVIDIA's CUDA occupancy calculator. For volume processing, a 1:1 mapping of threads to voxels in the x and y direction may be used. The z direction may be handled by looping over the per voxel function with increasing z indices. The stride may be the z block size, which maintains thread spatial cohesion. Cuda now also supports a 3D grid of 3D blocks. Increased thread spatial cohesion, enhanced by cube-like block dimensions, can reduce cache misses and improve performance. All input array data may be cached, generally in textures, which in the case of the superposition can provide a ~2× improvement in performance. Shared memory may be used to cache the array of multi-resolution volume structures. Shared memory may also offer a performance improvement over registers for the multi-spectral TERMA calculation. A maximum number of 21 energy bins may be chosen as being both sufficient for high energy beams and free of bank conflicts.

TABLE 2

The average mean depositied dose error relative to $D_{max}$, the maximum deposited dose, for field sizes from 1 cm to 23 cm. Error is broken down by region with the penumbra region defined as having a dose gradient greater than 0.3 $D_{max}$ and the low dose region being below 0.2 $D_{max}$. Fields were square and size was defined at a depth of 10 cm Reference dose deposition was calculated using a tilted kernel sampled with 4608 rays. Pencil beam accuracy was approximated by truncating the superposition kernel at a 3 cm radius. An absolute dosimetry error of 2-5% is clinically acceptable (Ahnesjo, A., Aspradakis, M., Phys. Med. Biol. 44, R99-R155, 1999).

|  | High dose region | | | Penumbra region | | | Low dose region | | |
|---|---|---|---|---|---|---|---|---|---|
| # of Rays | 80 | 72 | 32 | 80 | 72 | 32 | 80 | 72 | 32 |
| Tiled | 0.15% | 0.13% | 0.34% | 0.22% | 0.13% | 0.30% | 0.21% | 0.14% | 0.25% |
| Not-Tilted | 0.37% | 0.38% | 0.53% | 0.79% | 0.73% | 0.73% | 0.43% | 0.39% | 0.44% |
| Multi-Resolution | 0.64% | 0.55% | 0.76% | 0.76% | 0.78% | 0.81% | 0.37% | 0.39% | 0.38% |
| Pencil Beam | 5.92% | 5.98% | 5.83% | 2.77% | 2.81% | 2.69% | 1.68% | 1.69% | 1.68% |

Figure 8A:
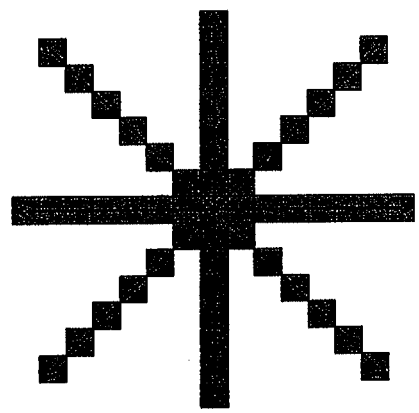
FIGS. 8A and 8B show the diagrams of the memory access patterns according to the conventional uniform sampling and a small field (5 mm) dose deposition slice calculated, respectively.
Figure 8B:
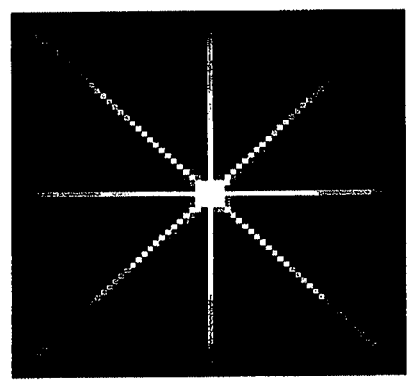
Figure 9A:
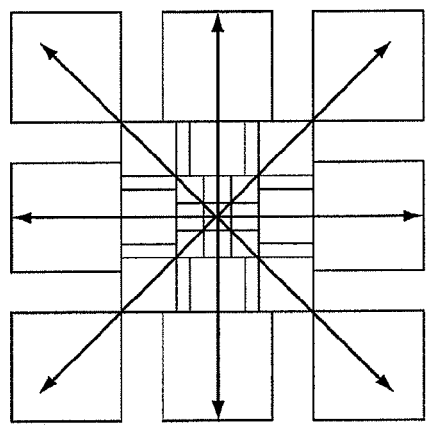
FIGS. 9A and 9B show the diagrams of the memory access patterns according to an embodiment of the present invention and a small field (5 mm) dose deposition slice calculated, respectively.
Figure 9B:
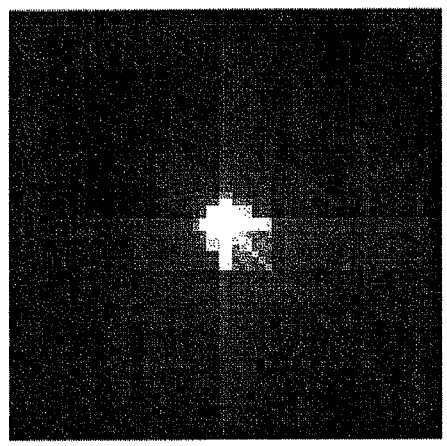

Small field artifacts, which occur when an entire beam is missed due to sparse ray sampling, can be reduced by using a multi-resolution grid according to some embodiments of the present invention. FIGS. 8A and 8B show the diagrams of the memory access patterns according to the conventional uniform sampling and a small field (5 mm) dose deposition slice calculated, respectively. FIGS. 9A and 9B show the diagrams of the memory access patterns according to an embodiment of the current invention using a multi-resolution grid and a small field (5 mm) dose deposition slice calculated, respectively.

However, larger step sizes can decrease the dose deposition kernel accuracy. Artifacts are introduced when neighbouring voxels transverse different coarse resolution voxels. It is noted that our implementation is inherently isotropic which tends to decrease the benefit of non-uniform angle sampling.

The multi-resolution algorithm can be implemented using a volumetric mip-map (Williams, L., SIGGRAPH Comput. Graph. 17, 3, 1-11, 1983), as it is both efficient to calculate and has good cache performance. Resolution changes may be limited to a maximum of once per step and may be only allowed to occur at voxel boundaries in the coarser resolution. This can prevent a TERMA voxel from contributing multiple times to the same dose voxel.

Several strategies can be used to optimize Compute Unified Device Architecture (CUDA) performance. CUDA's execution model is a 2D grid of 3D blocks of threads which execute a function (called a kernel). Each In both stages of TERMA computation and superposition according to an embodiment of the present invention, the standard fixed step size ray-cast algorithm may be replaced with an exact radiological path method, similar to line rasterization (Amanatides, J., Woo., A., Eurographics'87, Conference Proceedings, 1987).

Figure 10:
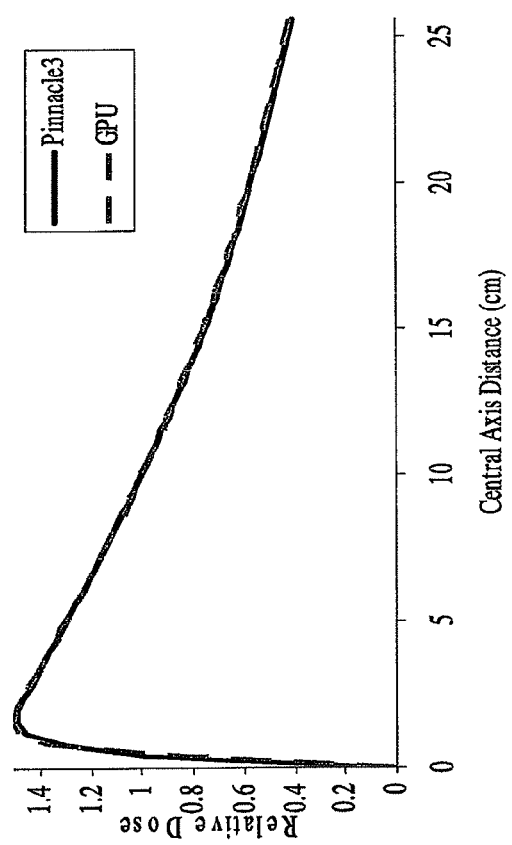
FIG. 10 shows absorbed dose patterns along the central axis calculated by a commercial Pinnacle system (Philips Radiation Oncology Systems Madison Wis.) and an embodiment of the present invention, each normalized at a depth of 10 cm.
Figure 11:
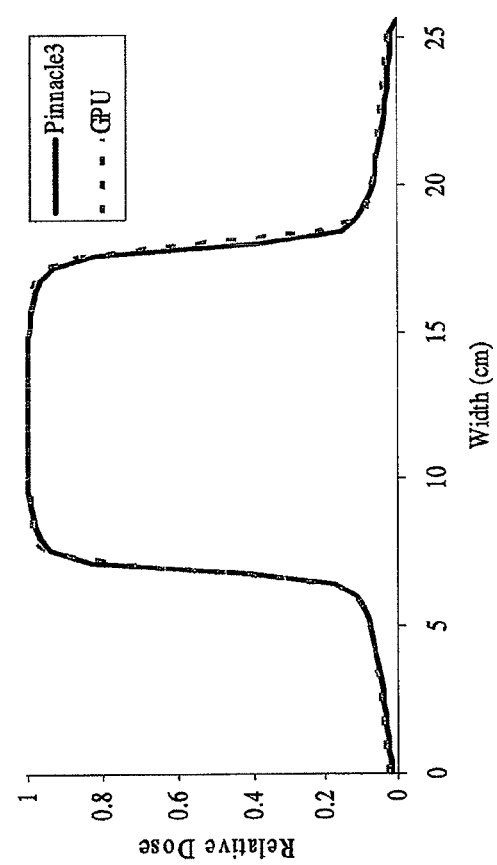
FIG. 11 shows absorbed dose profiles calculated by a commercial Pinnacle system (Philips Radiation Oncology Systems Madison Wis.) and an embodiment of the present invention at a depth of 10 cm, each normalized at the midpoint.

FIG. 10 shows absorbed dose patterns along the central axis calculated by a commercial Pinnacle system (Philips Radiation Oncology Systems Madison Wis.) and an embodiment of the present invention, each normalized at a depth of 10 cm. FIG. 11 shows absorbed dose profiles calculated by a commercial Pinnacle system and an embodiment of the present invention at a depth of 10 cm, each normalized at the midpoint.

Quantitative analysis of a transport algorithm, such as superposition/convolution, can be complicated by a strong dependence on the incidence fluence from the source model of the radiation source for the radiation treatment (Mohan, R., Chui, C., Lidofsky, L., Med. Phys. 12, 592-597, 1985; McNutt, T. R.: Dose Calculations, Philips white paper). The source model in turn needs to be optimized to minimize the error between measured dose and calculated dose. Thus, the source model often can mask errors in the transport algorithm. Furthermore, commercial systems may include a separate electron contamination model. In the preliminary experiments conducted using an embodiment of the current invention, only a simple source model is considered. The preliminary experiments yield results similar to those using the modeling parameters of a commercial treatment planning system, while providing an order of magnitude speed improvement as shown in Table 3.

TABLE 3

Comparison of dose engine performance on cube water phantoms. Rates reported in volumes per second (VPS). The tilting 32-ray kernel is more accurate than the non-tilting 80-ray kernel (See Table 2). Adaptive multi-grid methods (not implemented) have a speed-up factor of ~2x on clinical data.

| Engine | Kernel Type | Rays | $64^3$ Time (s) | VPS | Speedup | $128^3$ Time (s) | Speedup |
|---|---|---|---|---|---|---|---|
| GPU | CCK, Tilting | 72 | 0.198 | 5.051 | 41.8x | 2.801 | 33.7x |
| GPU | CCK, Non-tilting | 80 | 0.159 | 6.289 | 52.0x | 2.254 | 41.9x |
| GPU | CCK, Tilting | 32 | 0.086 | 11.628 | 96.1x | 1.246 | 75.8x |
| GPU | CCK, Multi-Resolution | 80 | 0.097 | 10.309 | 85.2x | 0.963 | 98.1x |
| GPU | CCK, Multi-Resolution | 32 | 0.042 | 23.810 | N/A | 0.411 | N/A |
| Pinnacle[3] | CK, Non-tilting | 80 | 8.268 | 0.121 | 1.0x | 94.508 | 1.0x |

In some experiments, clinical references were generated using the Pinnacle[3] (Philips—Madison, Wis.) treatment planning system commissioned on clinical data from a Varian 6EX linear accelerator, providing a dose deposition, TERMA, transmission array, spectra, mass attenuation tables and mono-energetic dose deposition kernels. All experiments were run on an AMD Opteron 254 (2 cores, 2.8 GHz). Timing experiments were repeated at least ten times with no other programs active, using the standard superposition/convolution engine.

Timing results for an embodiment of the present invention were repeated multiple times using the high performance hardware counter of the CPU. Experiments were performed on a 3 GHz Pentium 4 with a single NVIDIA GeForce GTX 280. The 80-ray kernels used 10 zenith by 8 azimuth directions angles. The 32-ray kernels used 4 zenith by 8 azimuth directions. The tilting 72-ray kernel used 6 zenith by 12 azimuth directions, which provided higher accuracy than the 80-ray kernel (See Table 3). Total dose engine performance was determined from the sum of the source model, TERMA and superposition performance, excluding reusable calculations such as the flattening filter texture and the TERMA attenuation volume.

All tests were performed on a cube water phantom with a side length of 25.6 cm. Tests were performed on a volume with $64^3$ voxels, representative of standard clinical workload, and an additional high resolution volume with $128^3$ voxels. The multi-resolution superposition approach as an embodiment of the present invention, utilizes volumetric mip-maps and can performed 2-3 times faster than traditional superposition and performance scaled better to higher resolutions as shown.

Figure 12:
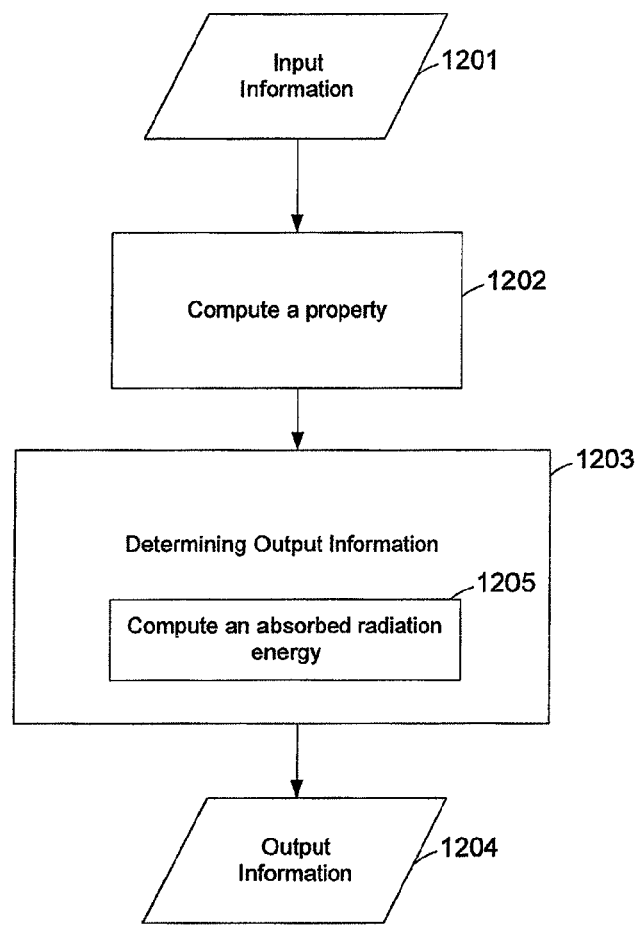
FIG. 12 illustrates a method according to another embodiment of the present invention.
Figure 13:
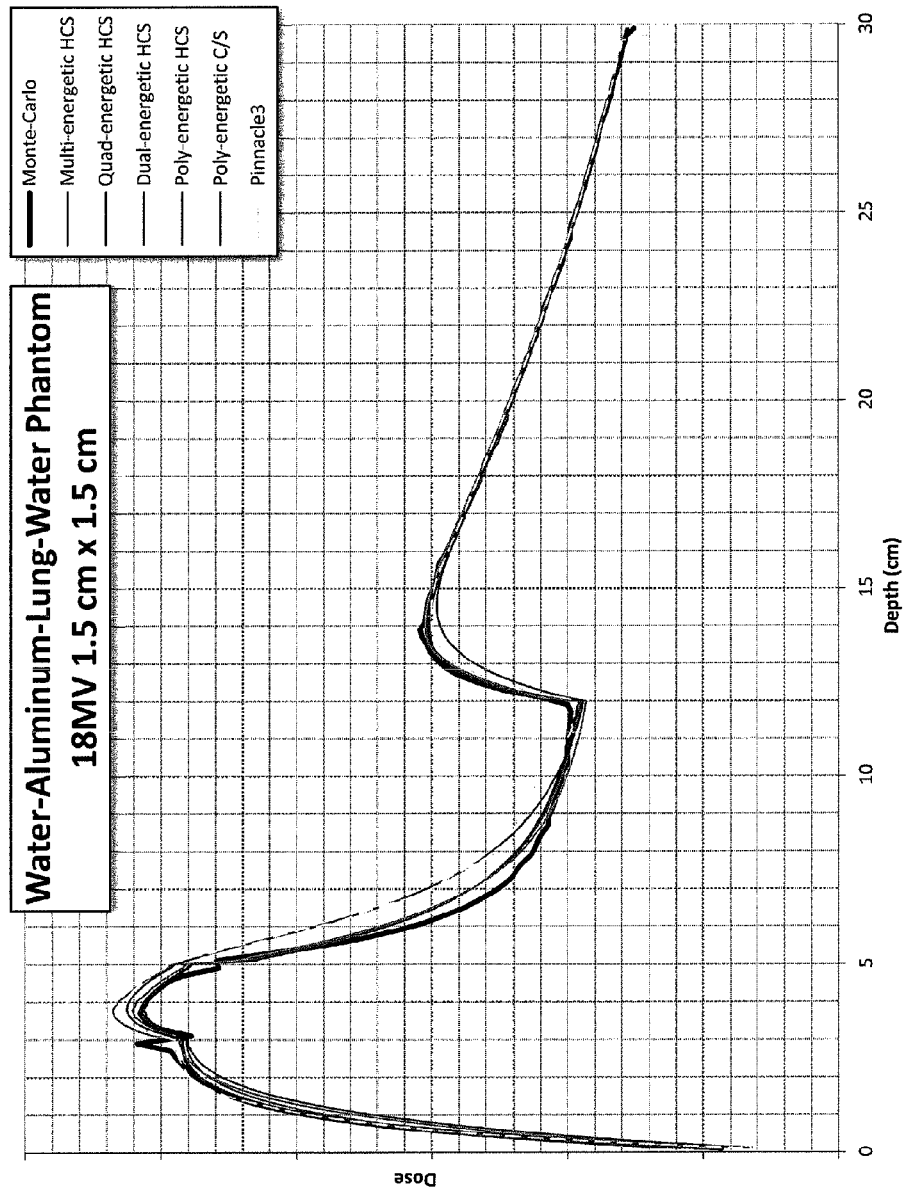
FIGS. 13-42 provide some examples of results that include Heterogeneity Compensated Superposition (HCS) according to an embodiment of the current invention.
Figure 14:
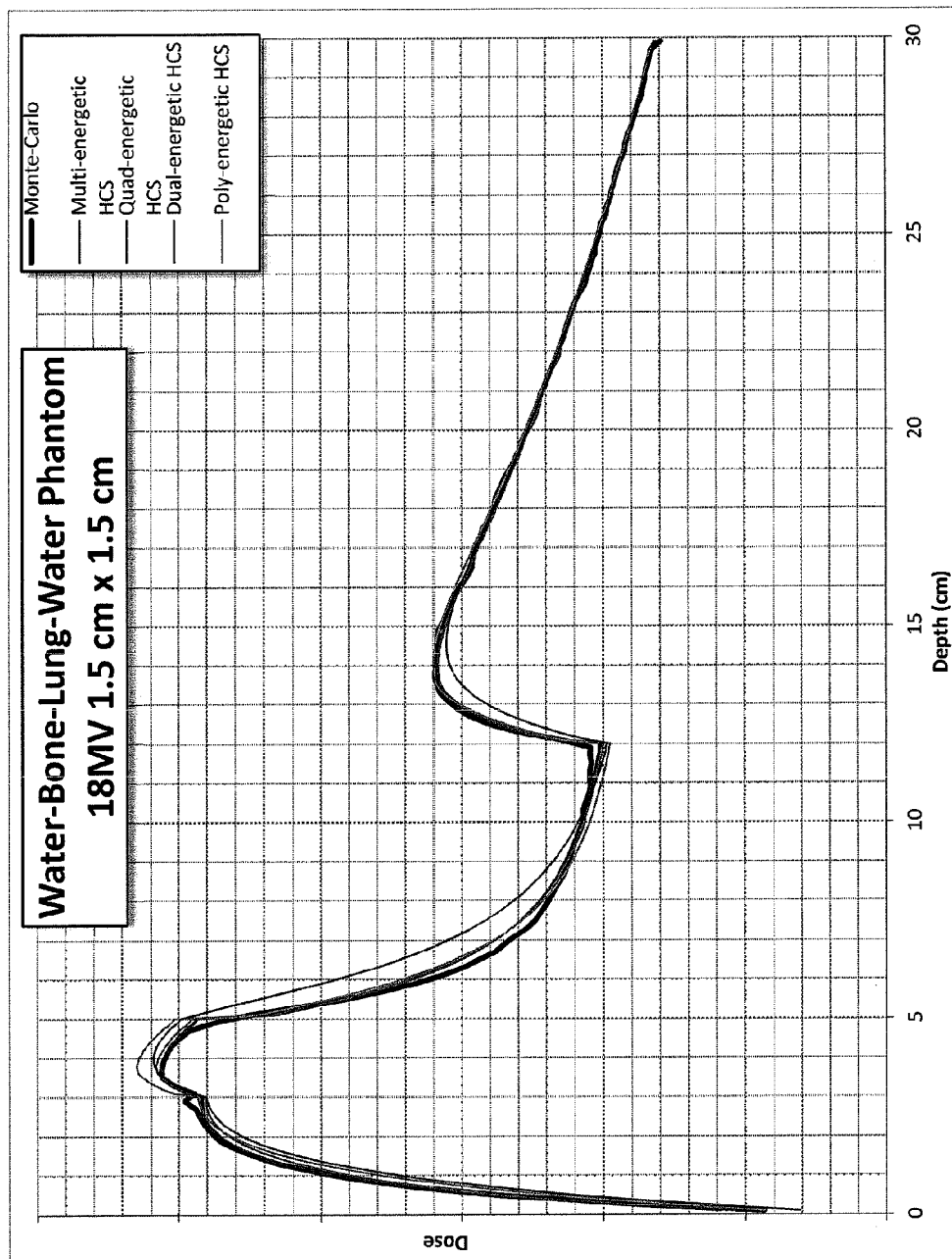
Figure 15:
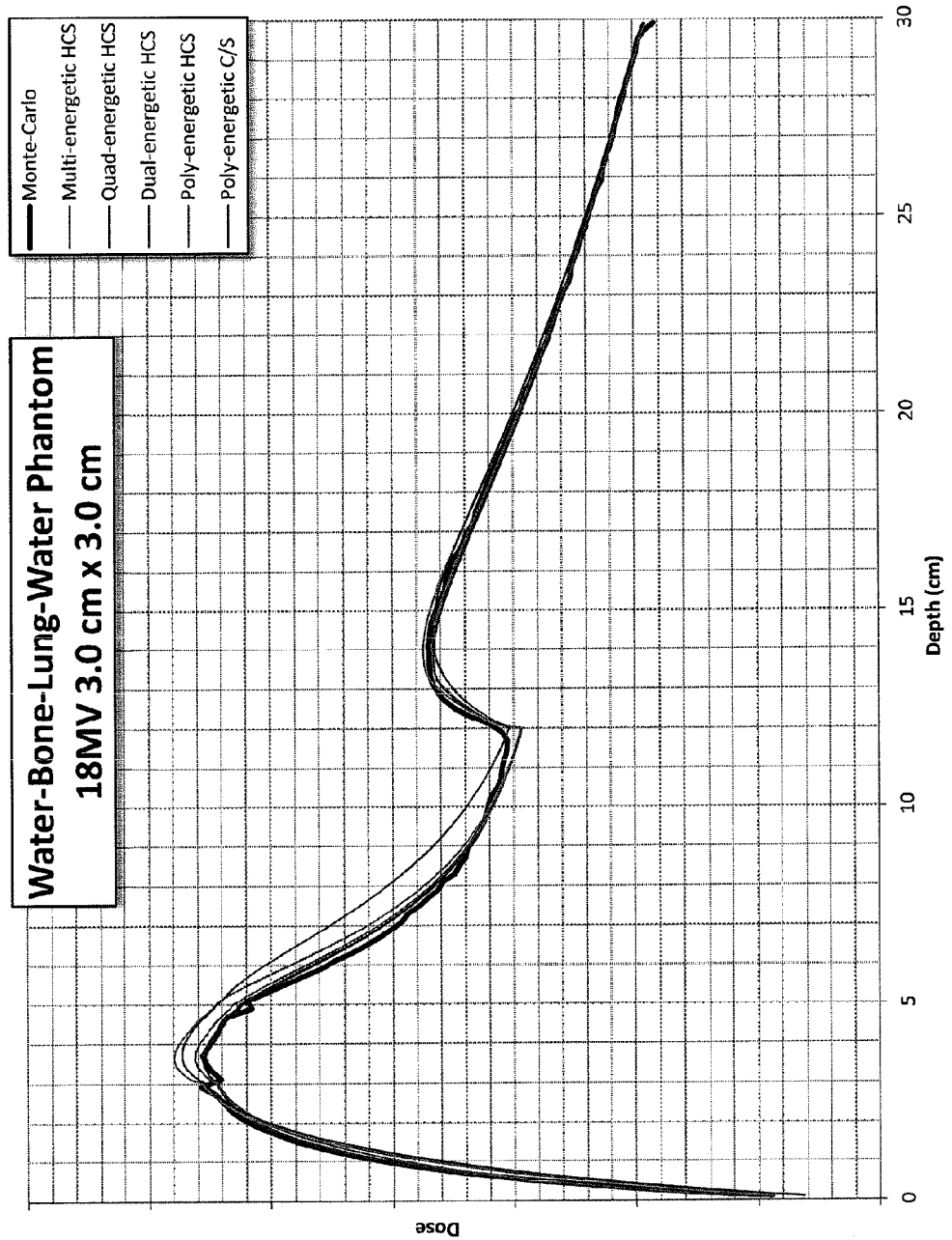
Figure 16:
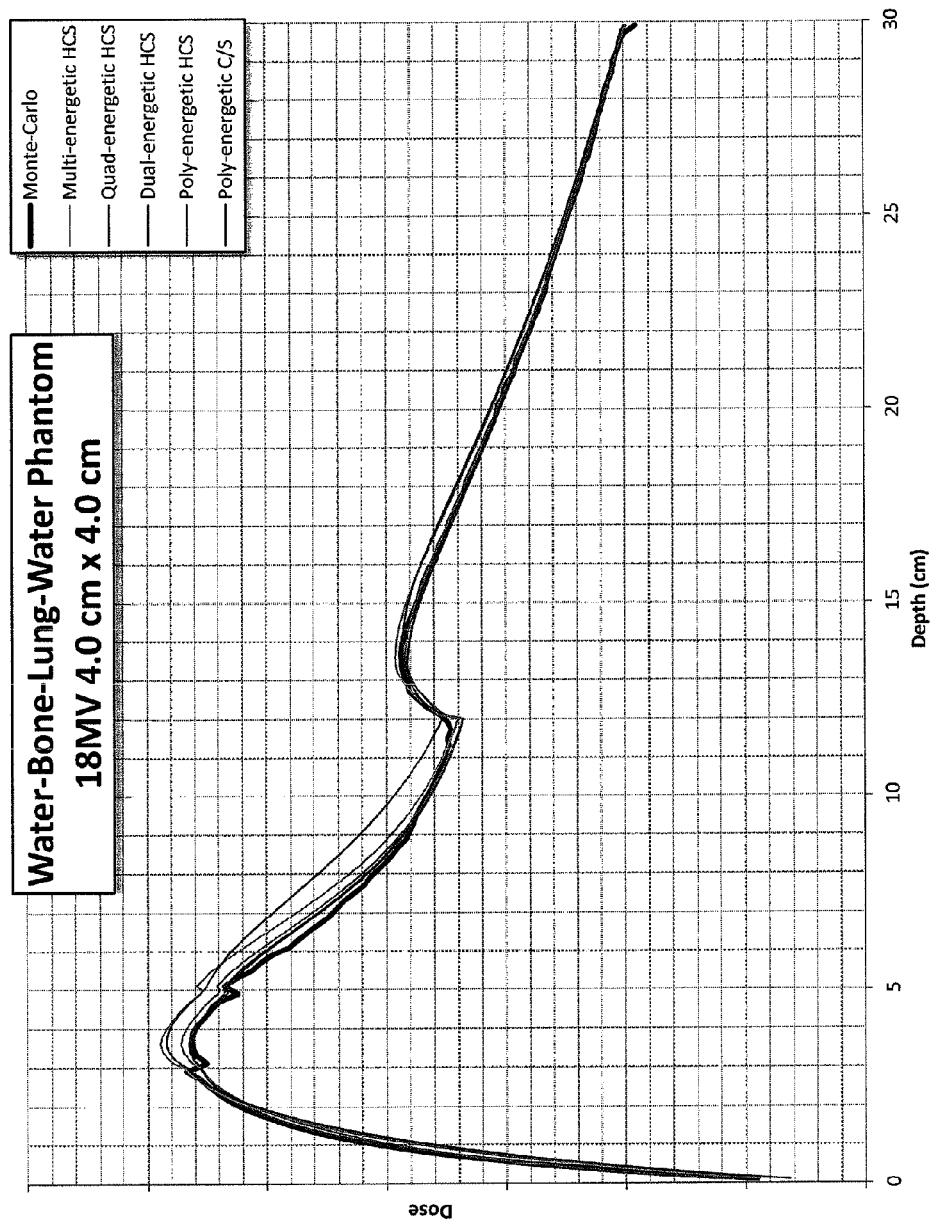
Figure 17:
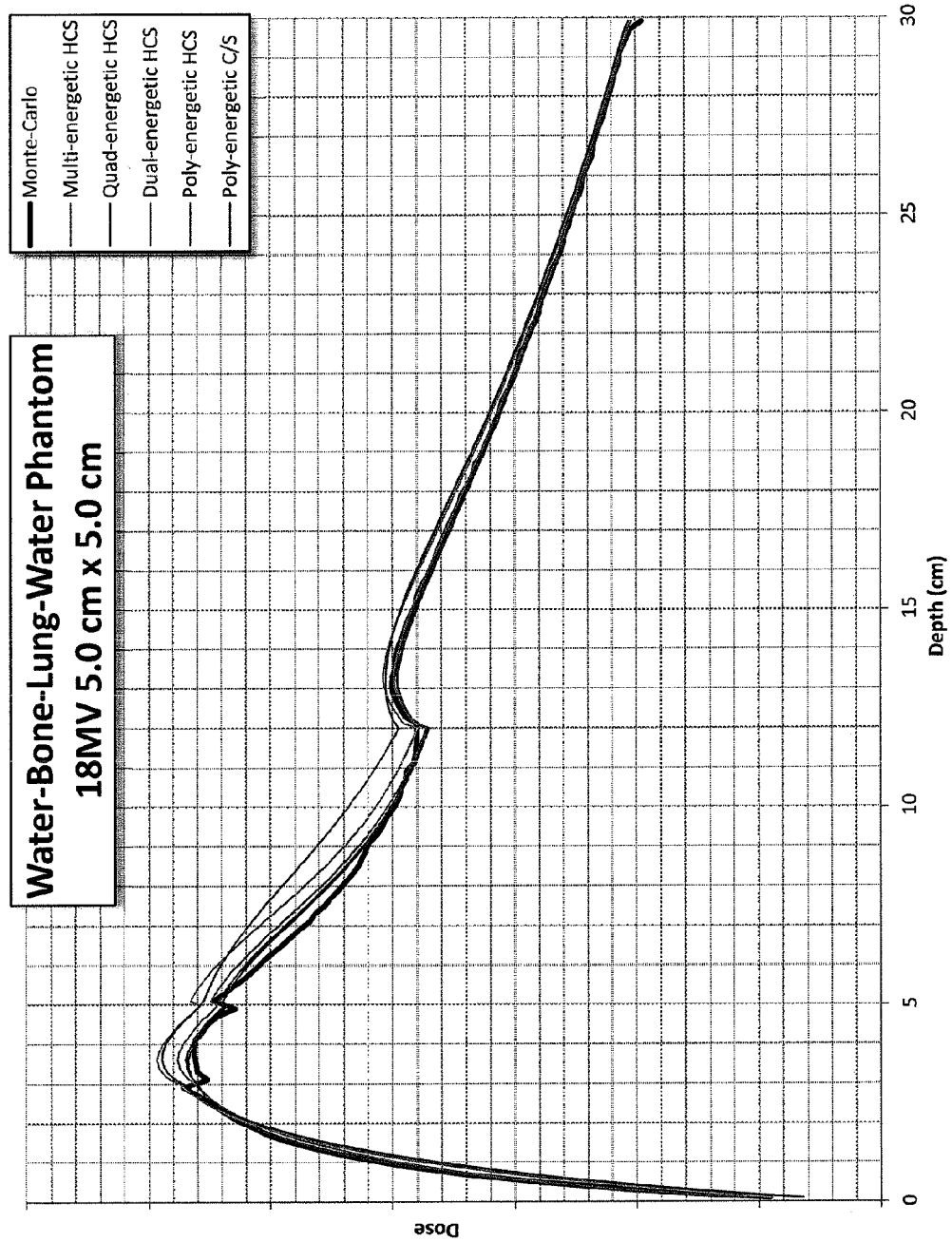
Figure 18:
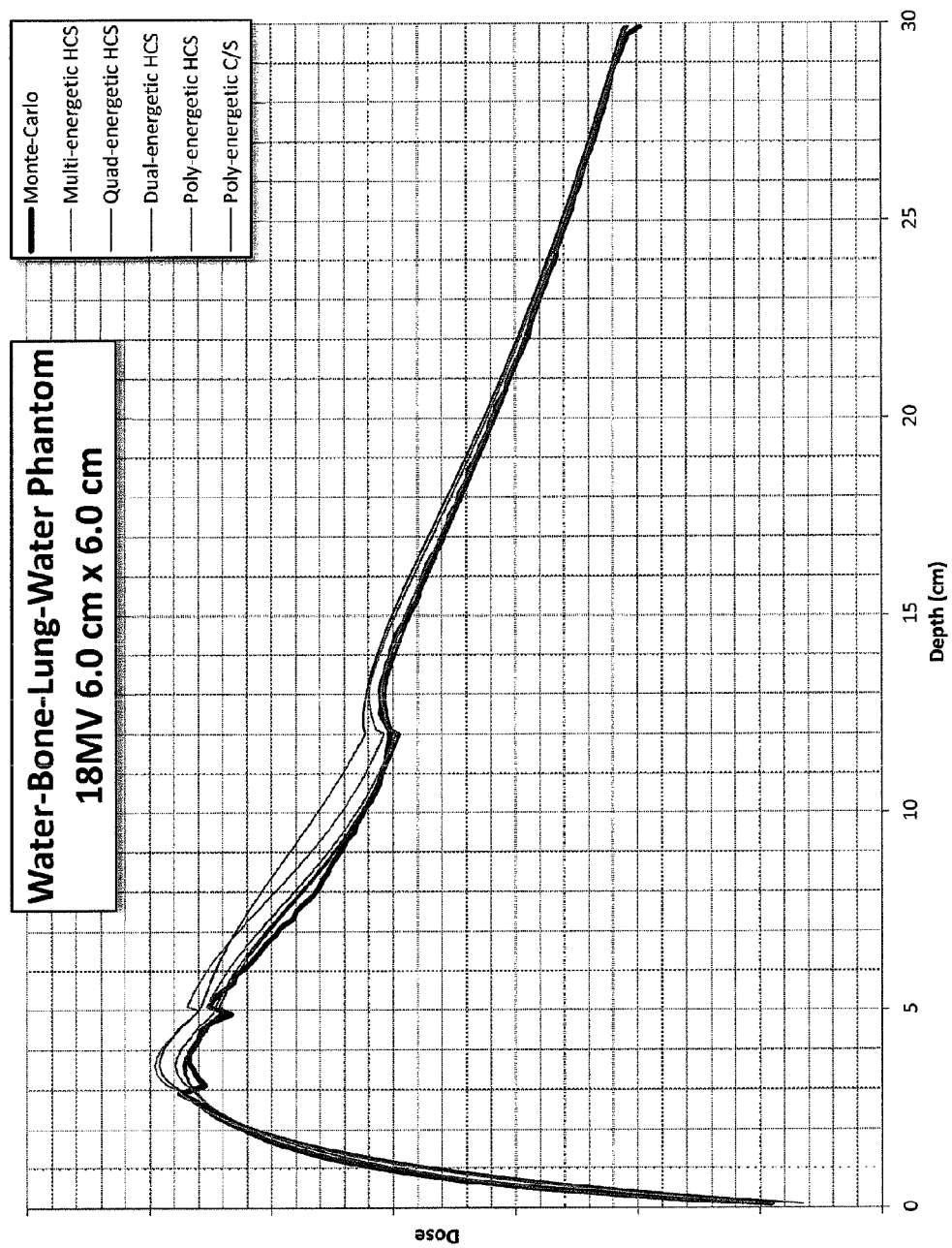
Figure 19:
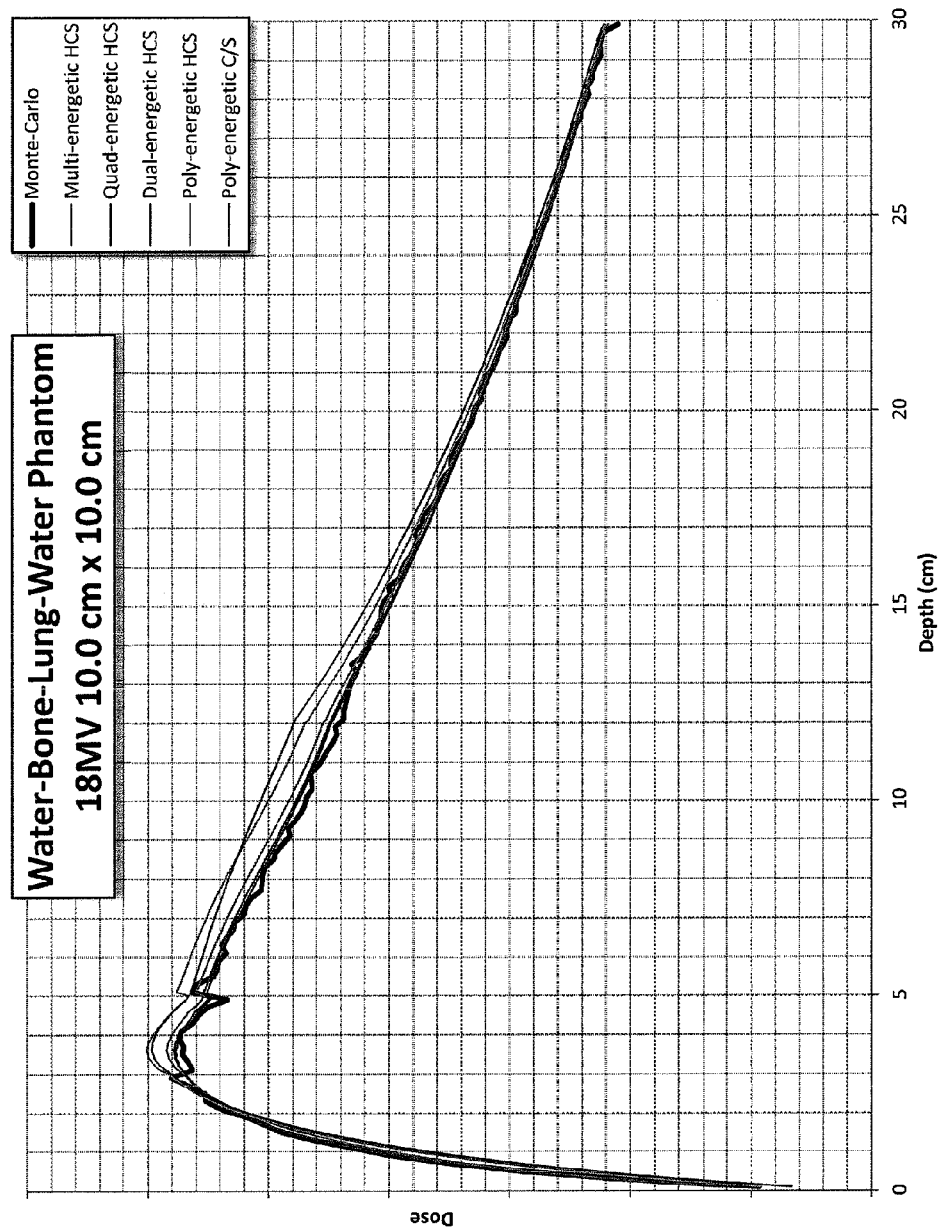
Figure 20:
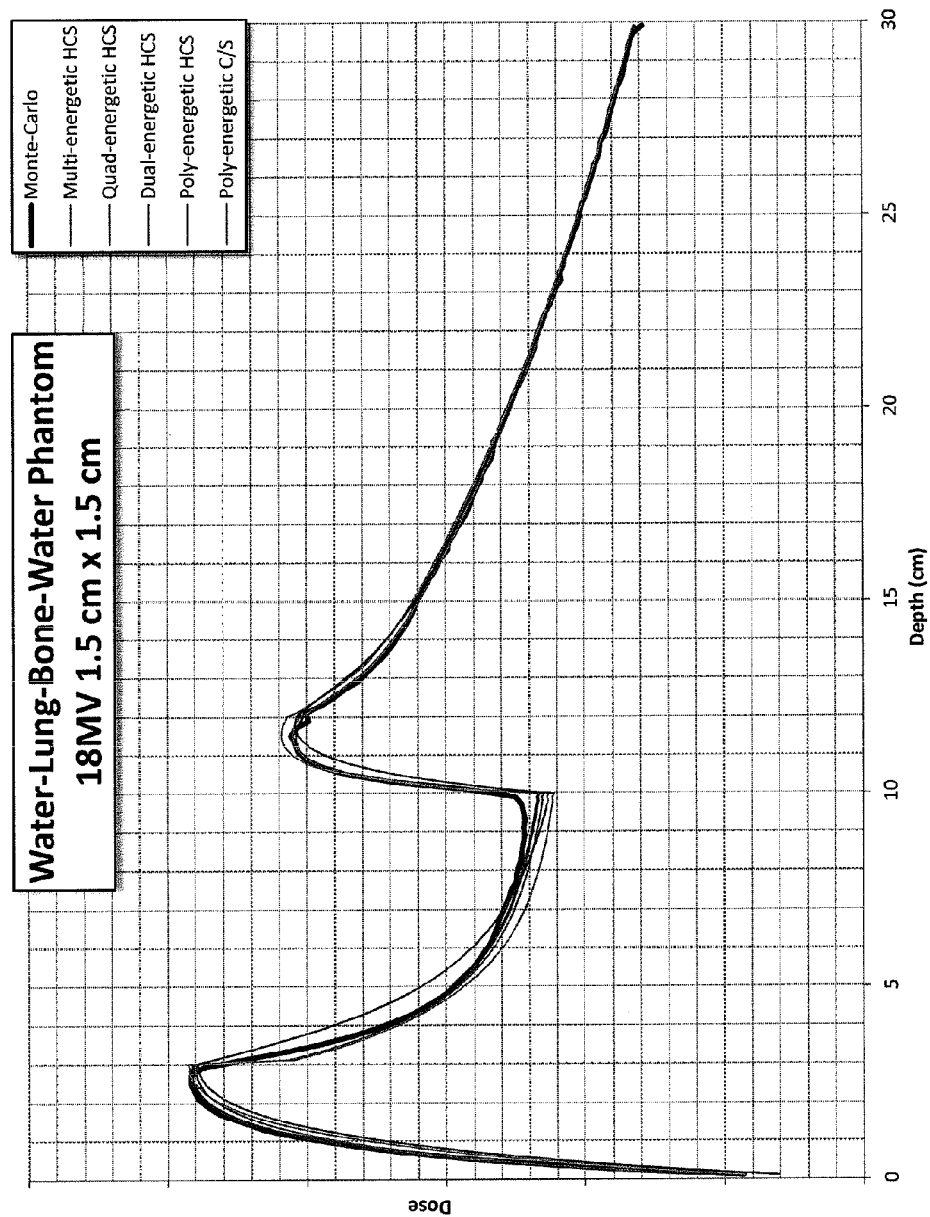
Figure 21:
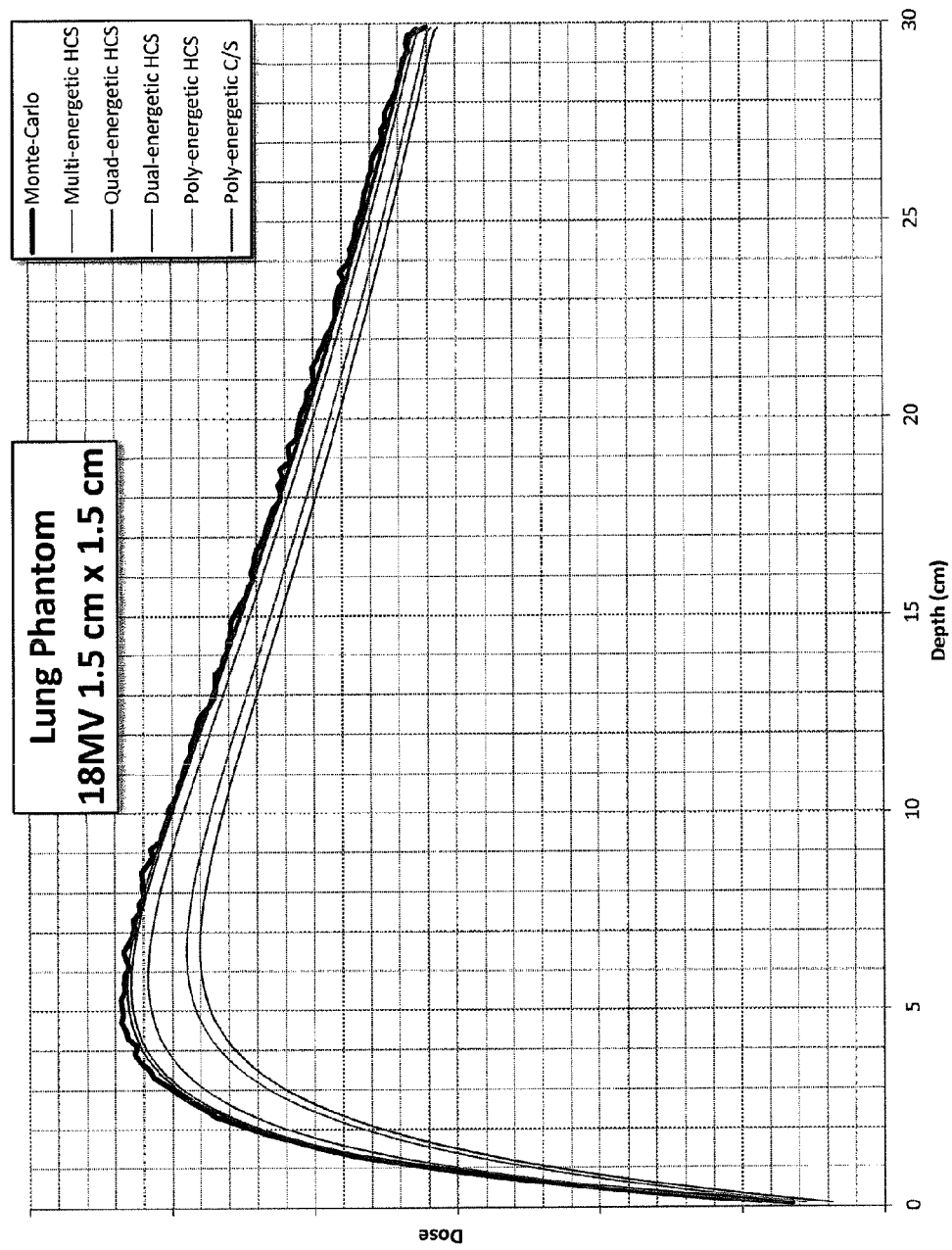
Figure 22:
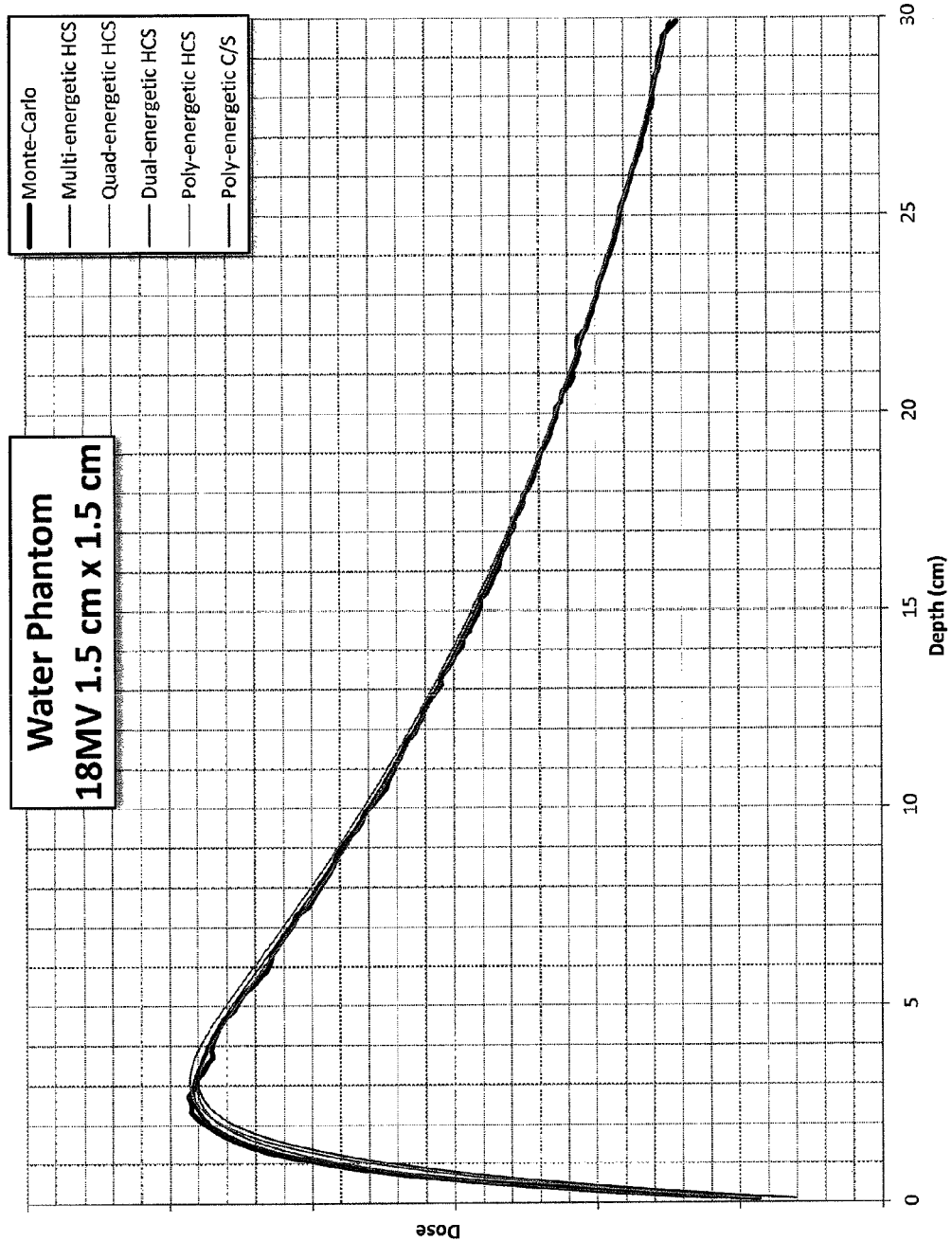
Figure 23:
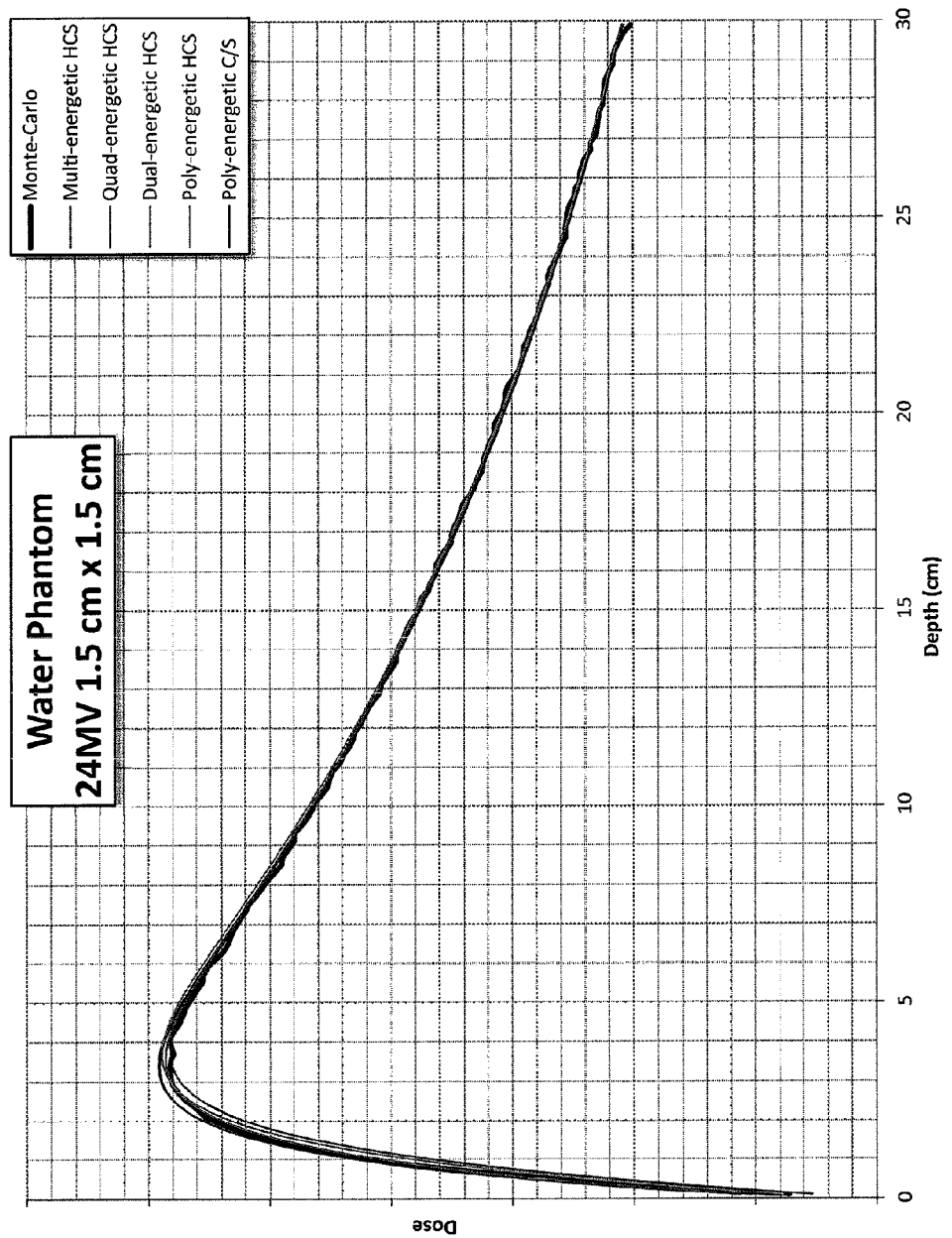
Figure 24:
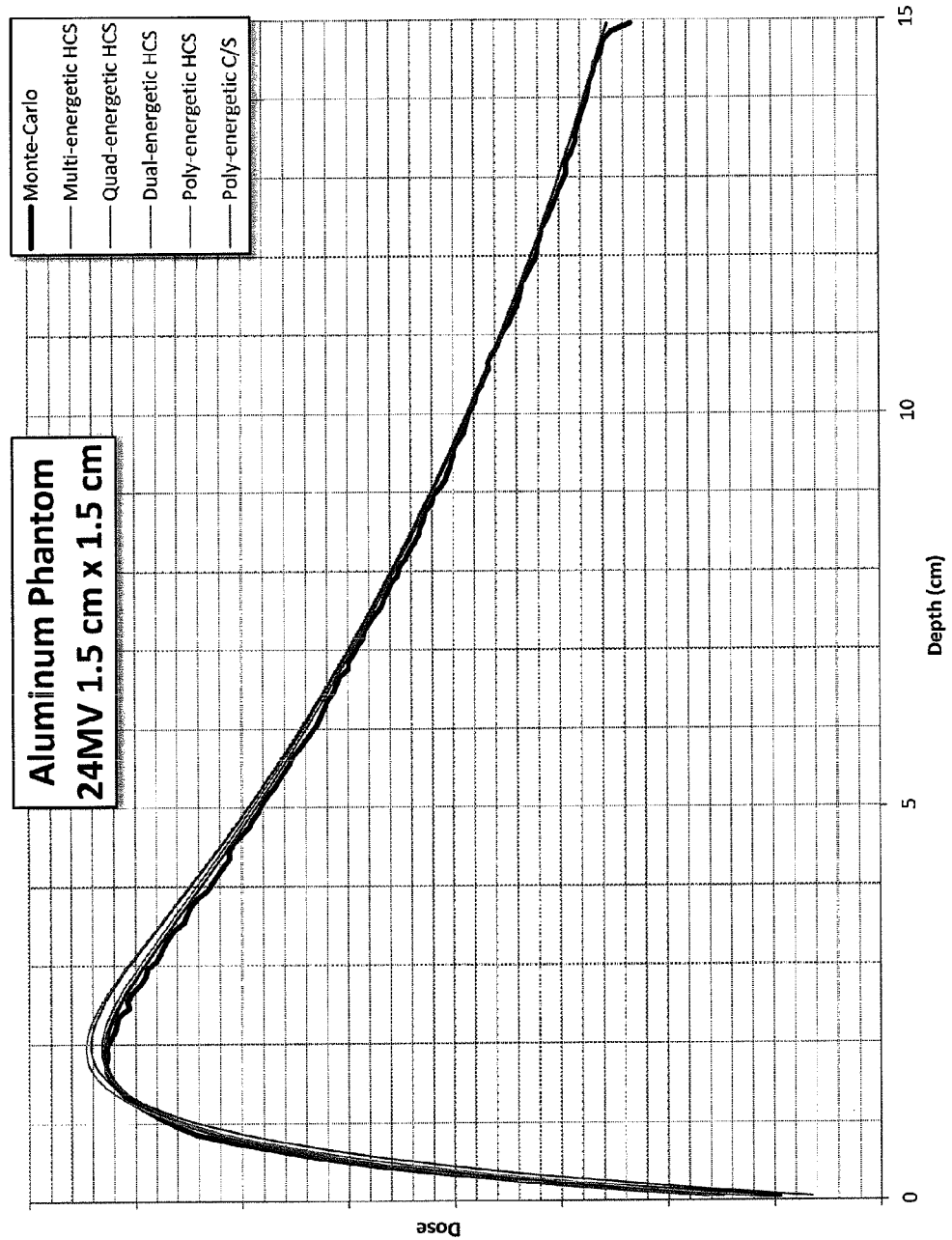
Figure 25:
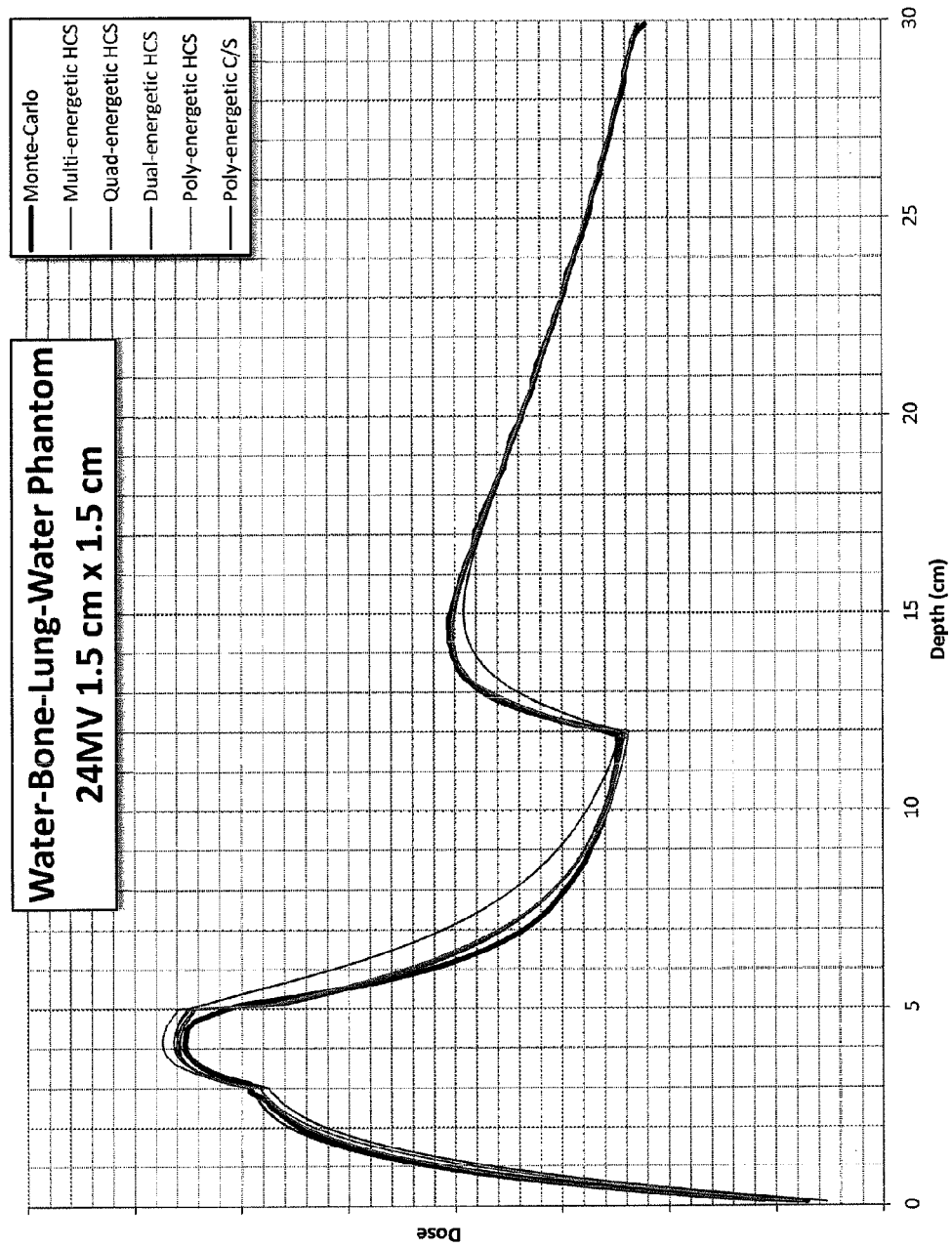
Figure 26:
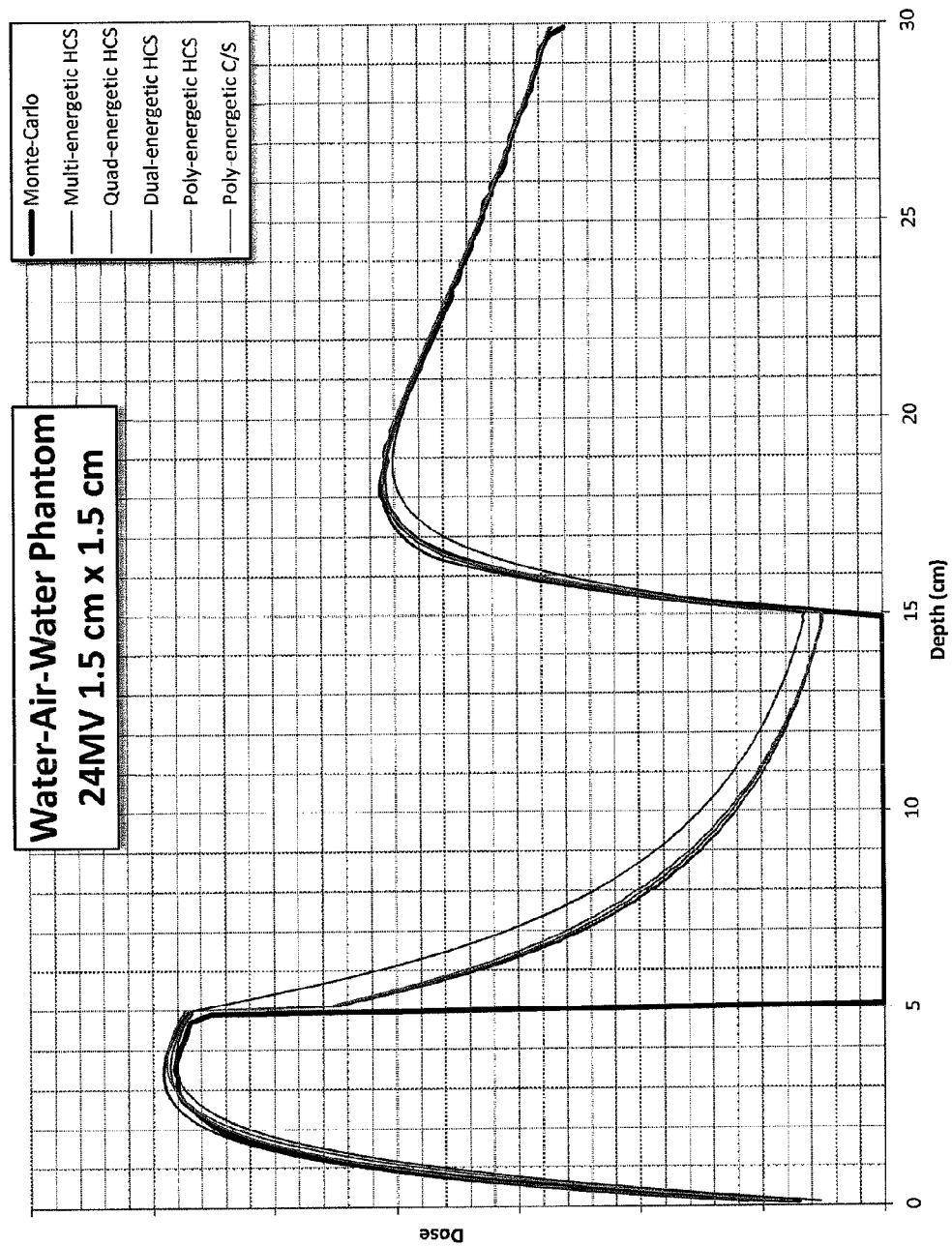
Figure 27:
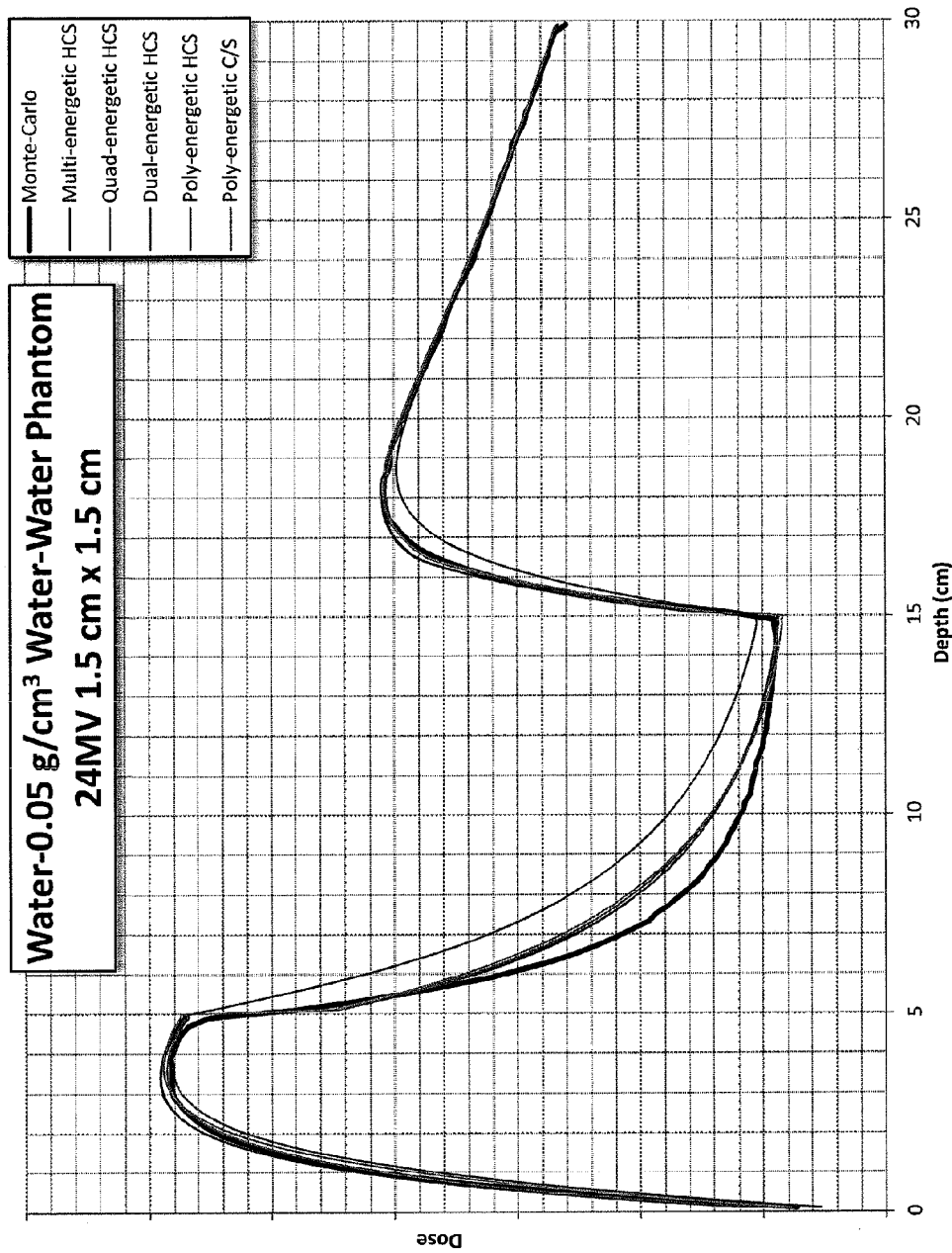
Figure 28:
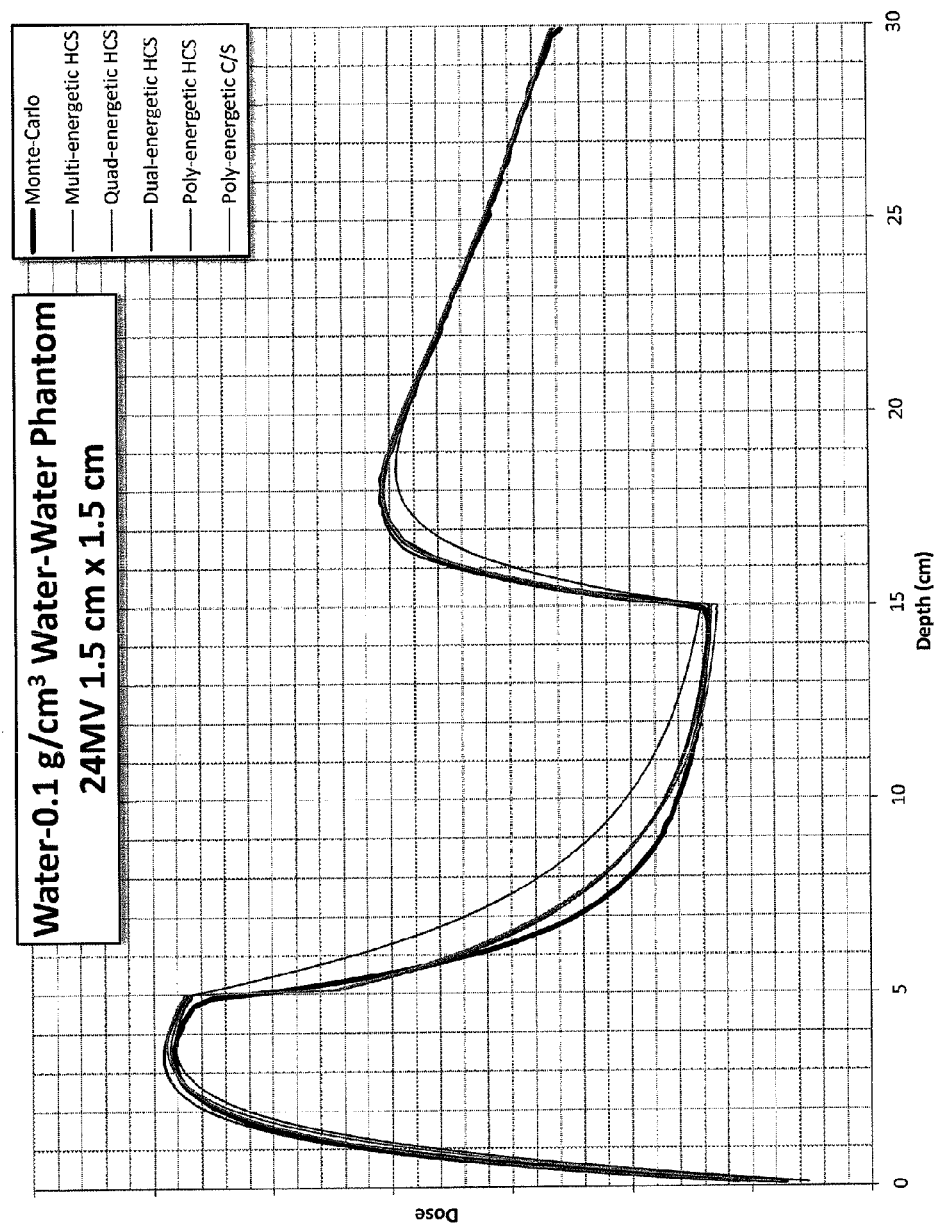
Figure 29:
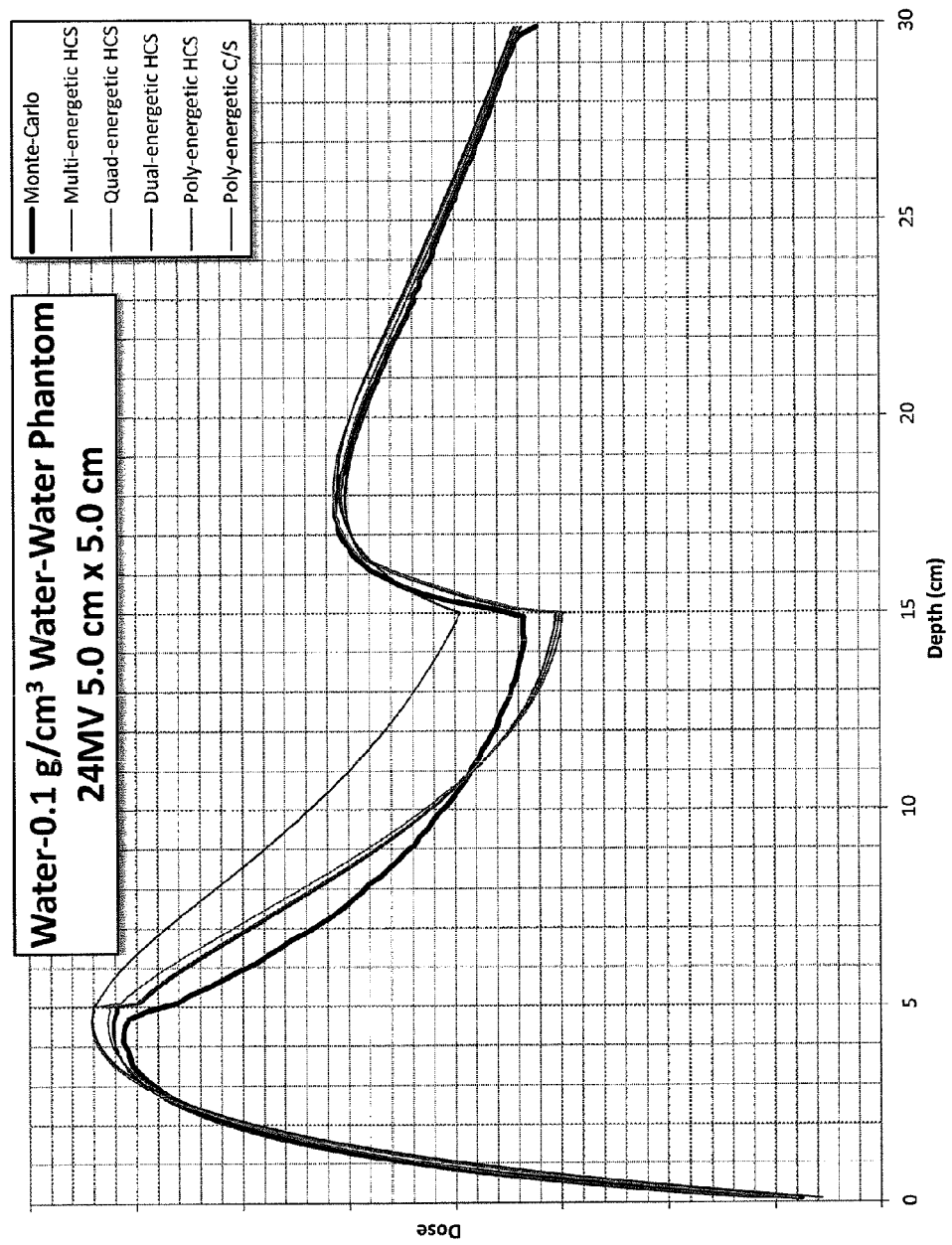
Figure 30:
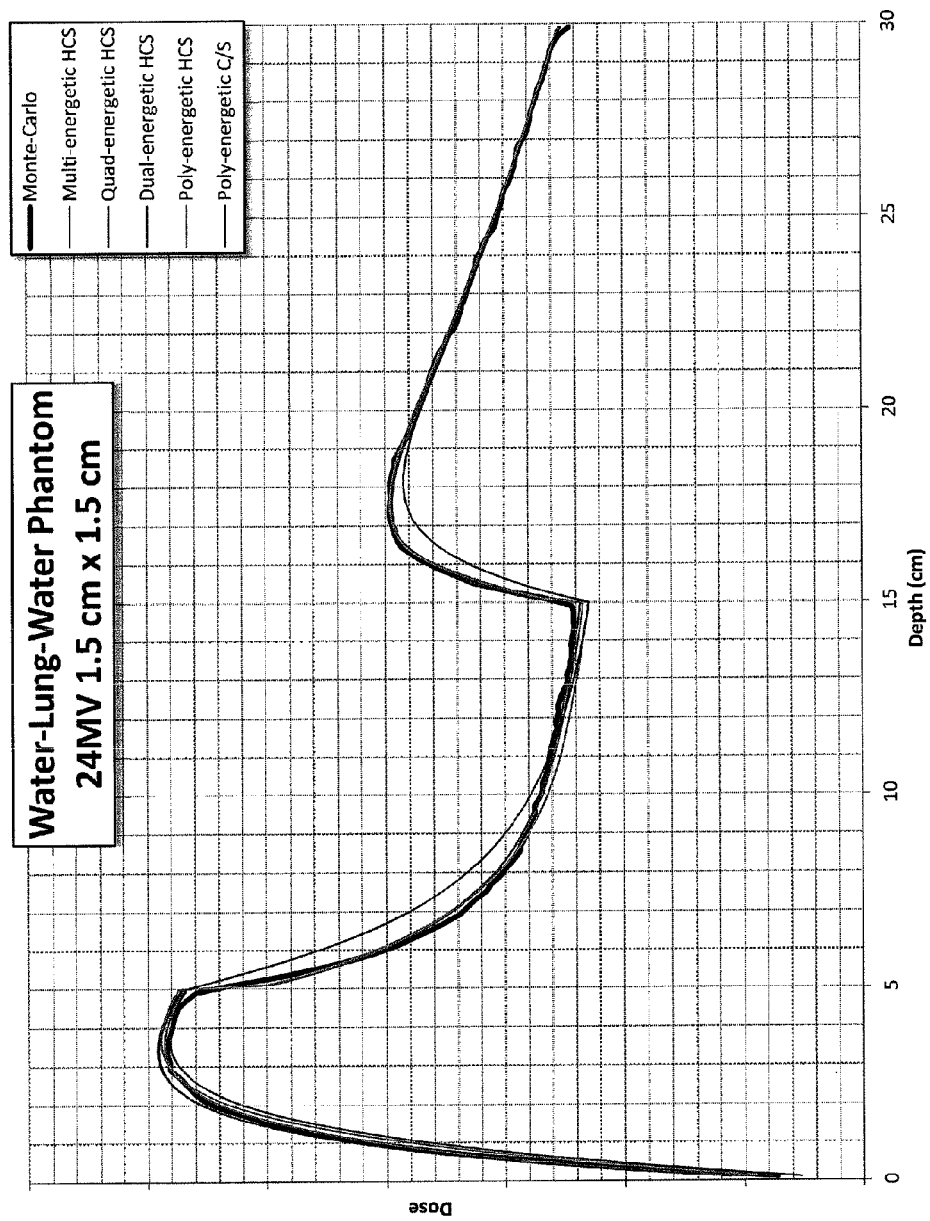
Figure 31:
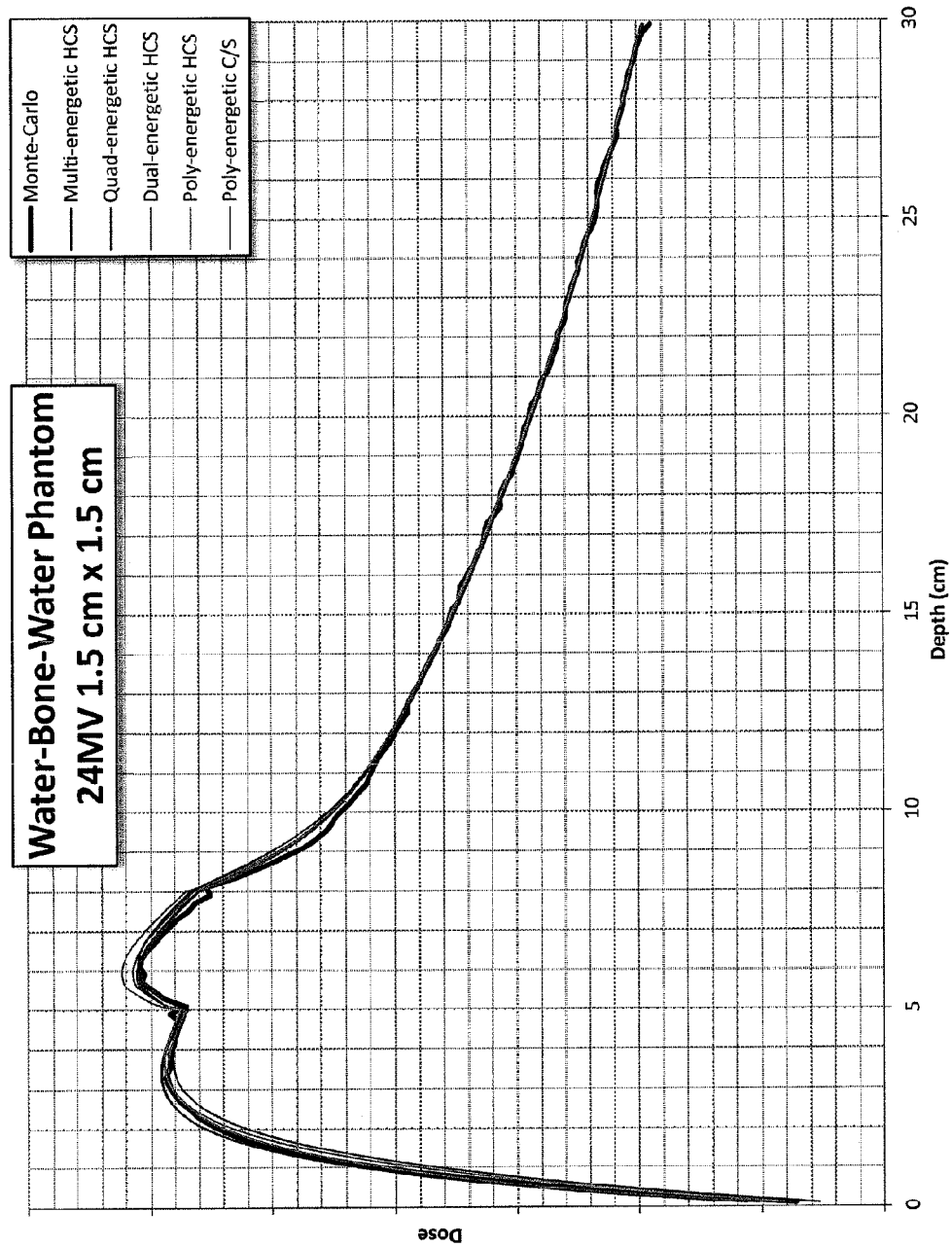
Figure 32:
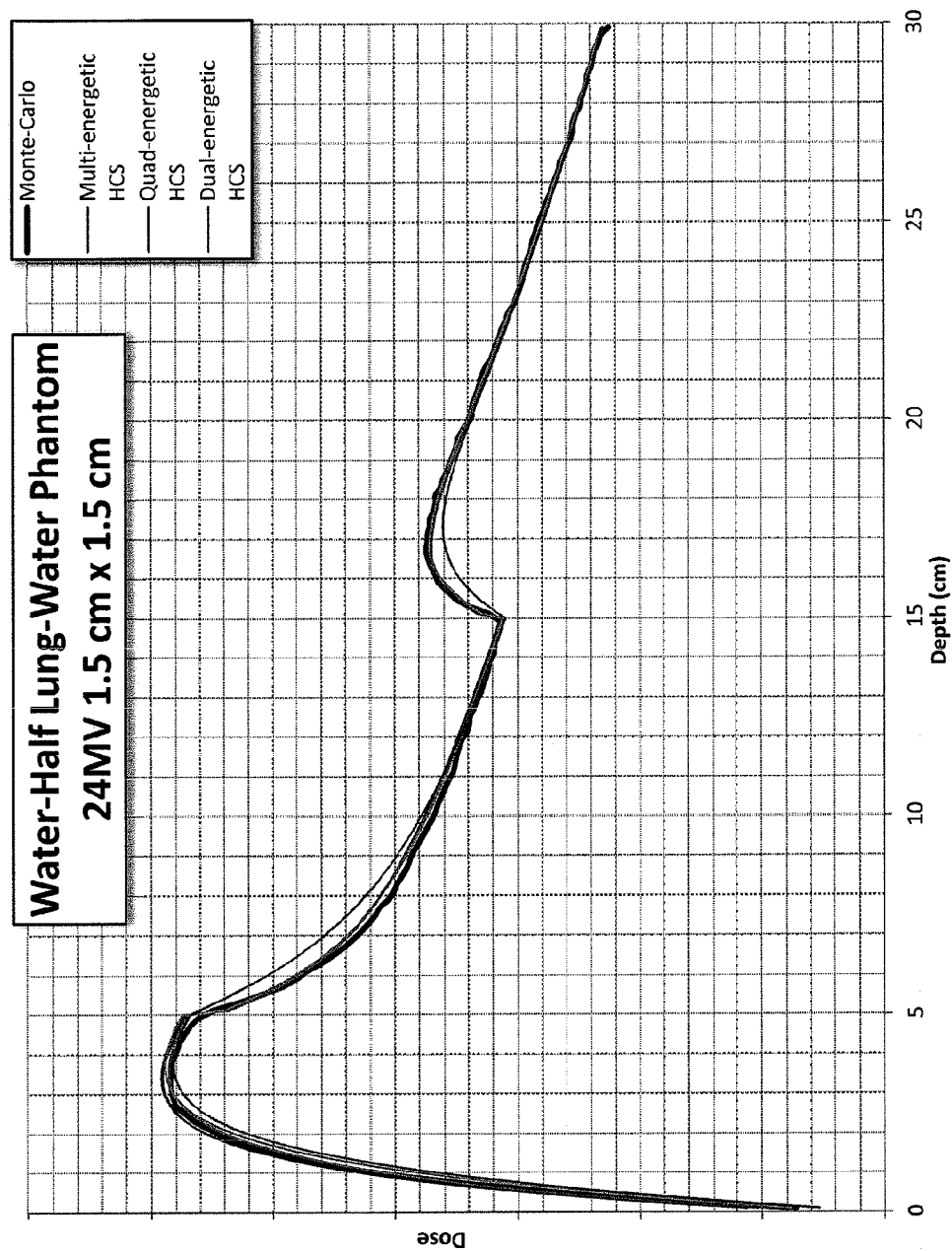
Figure 33:
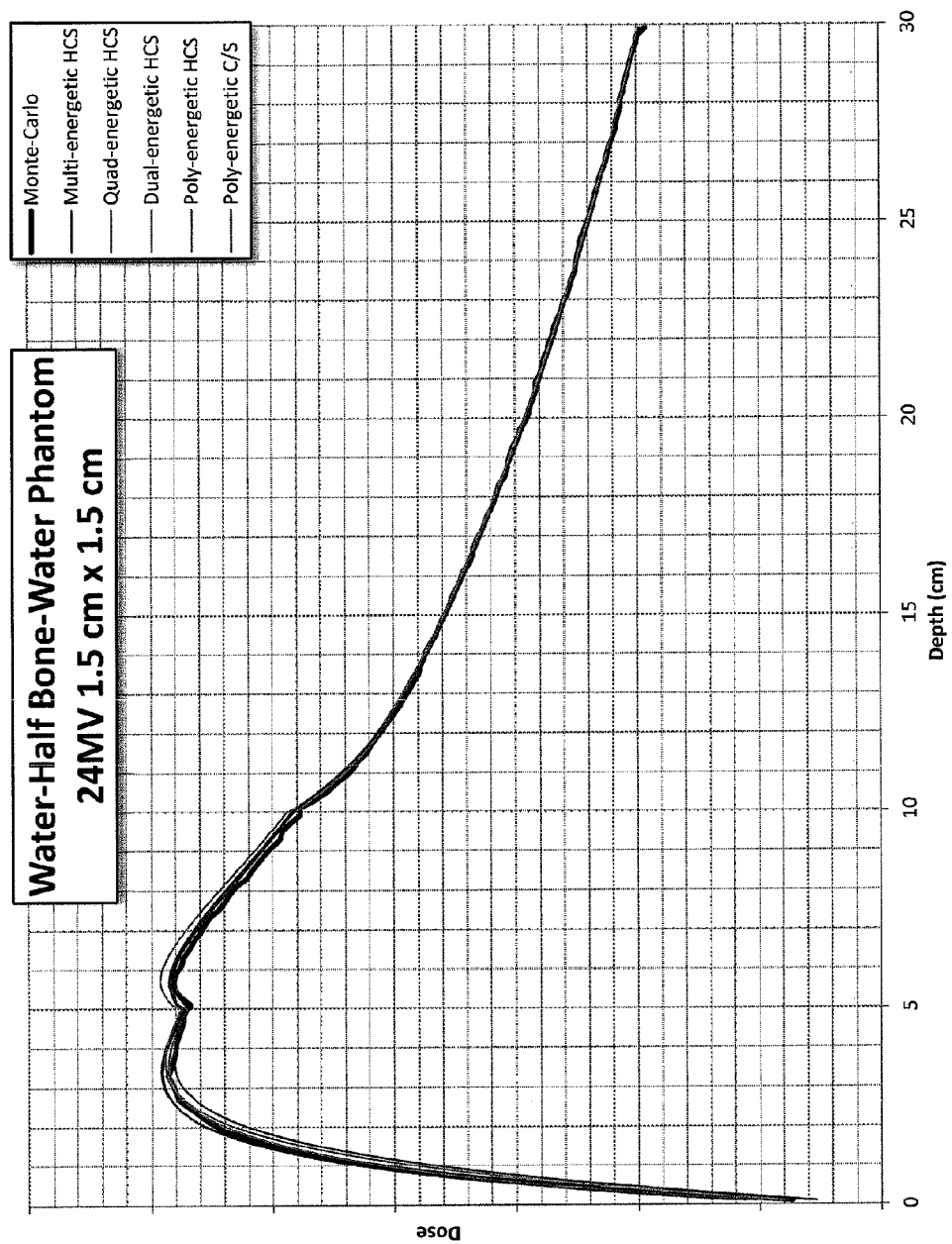
Figure 34:
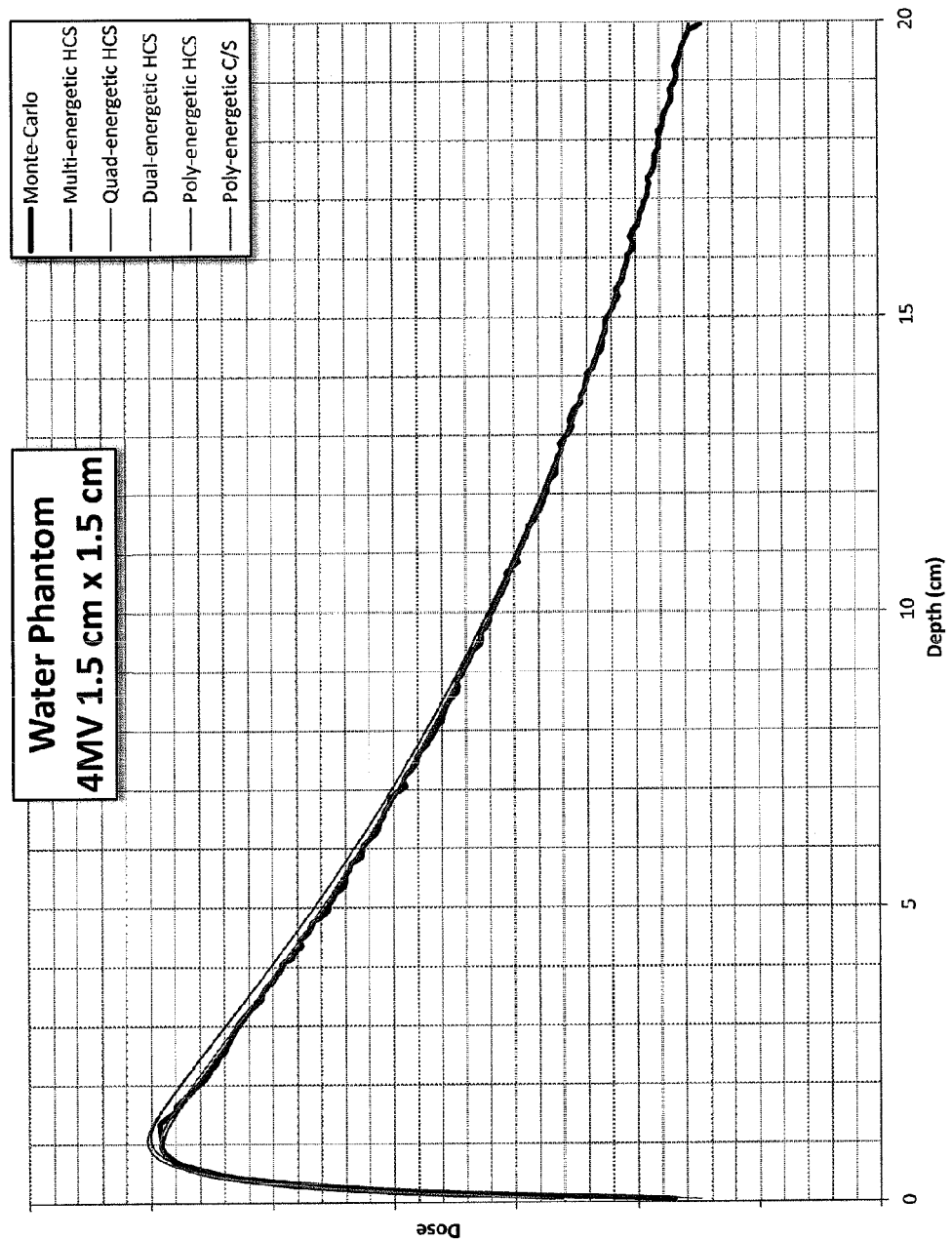
Figure 35:
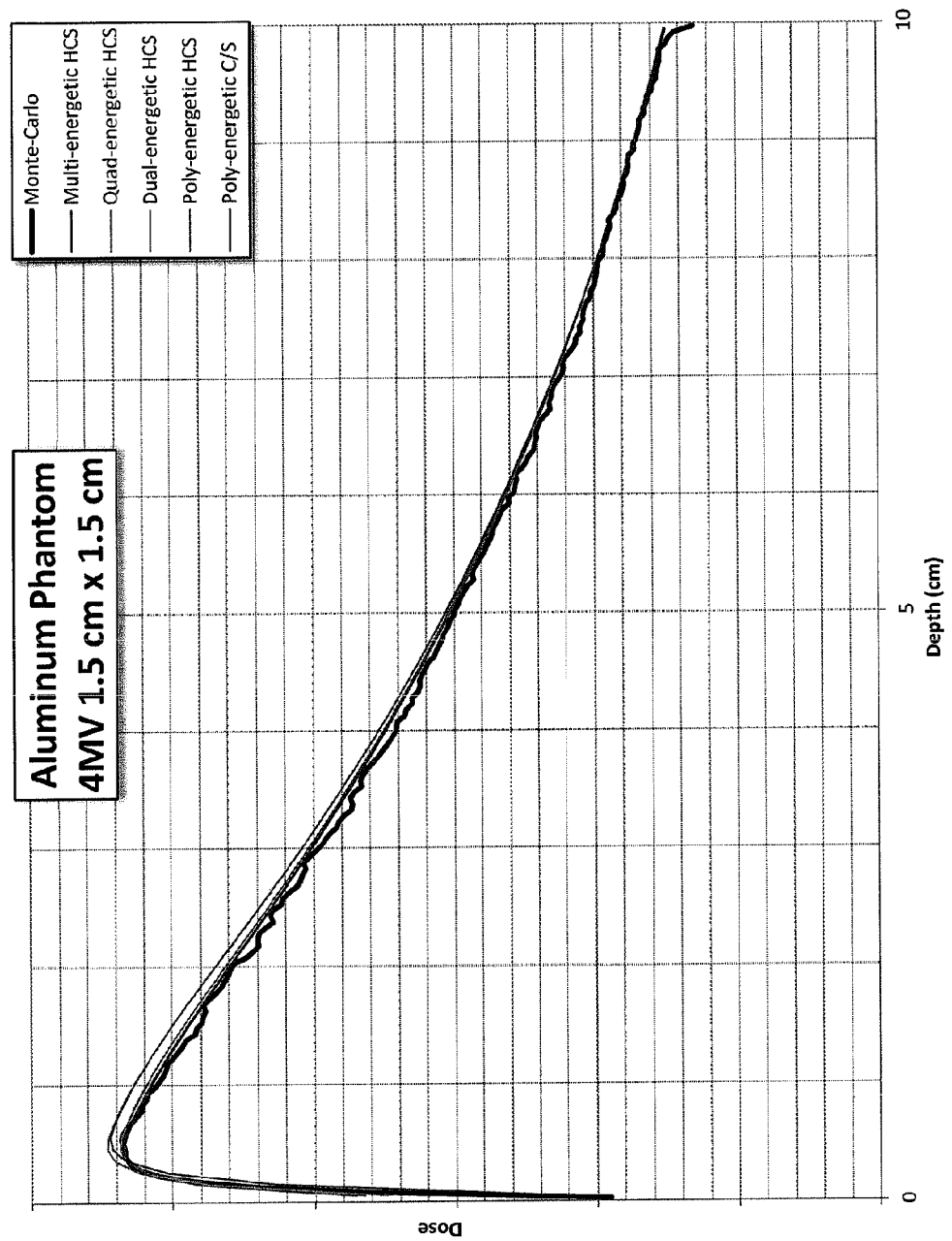
Figure 36:
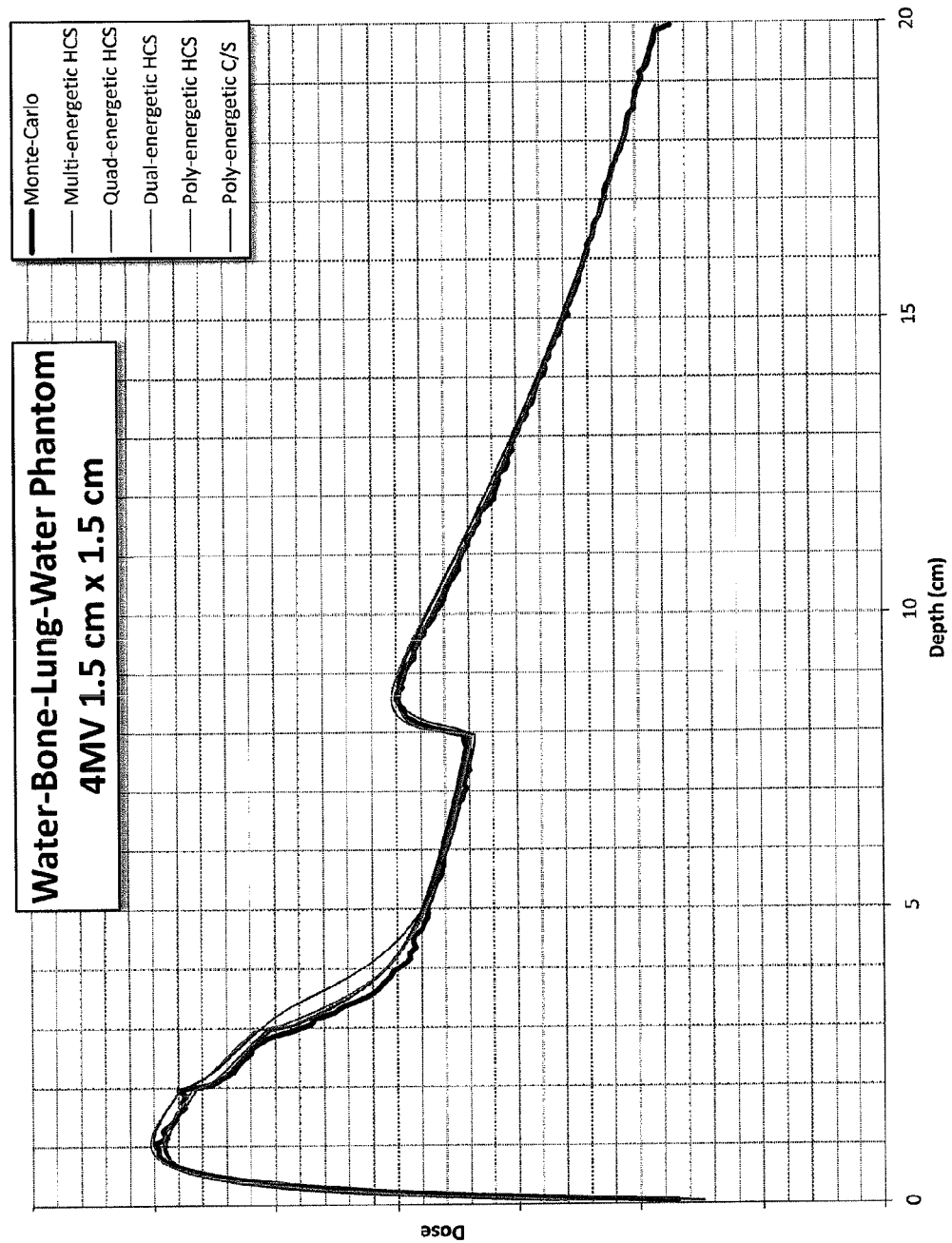
Figure 37:
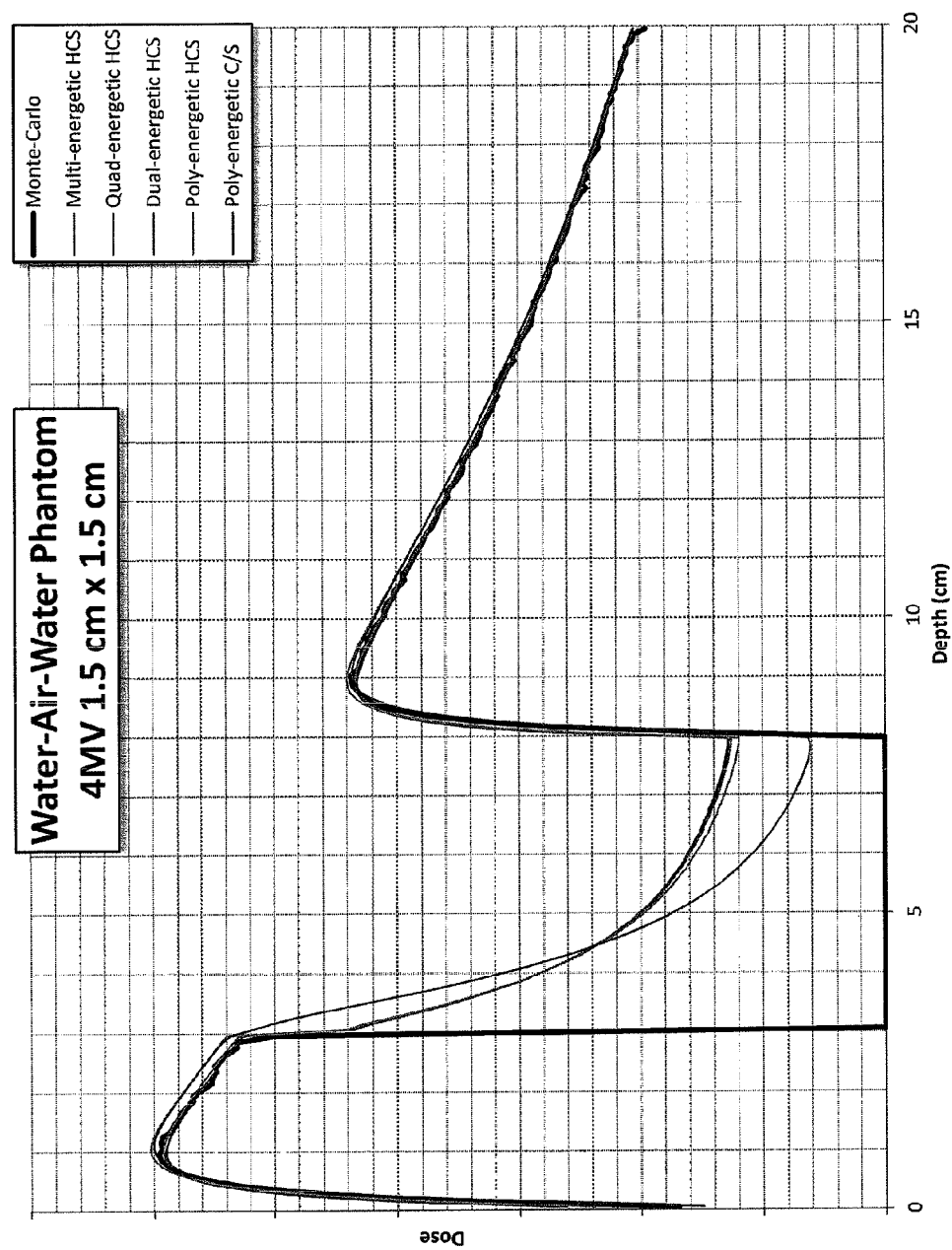
Figure 38:
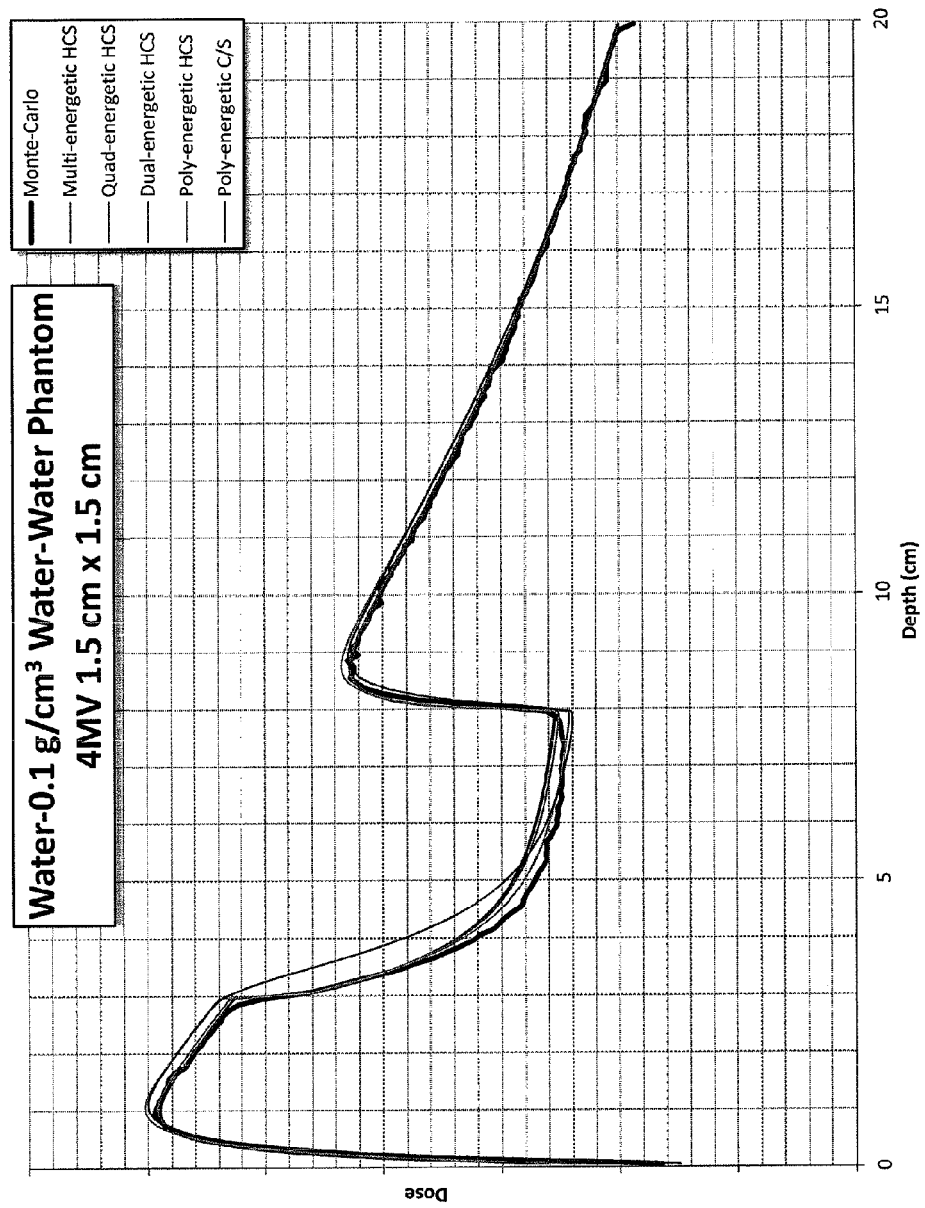
Figure 39:
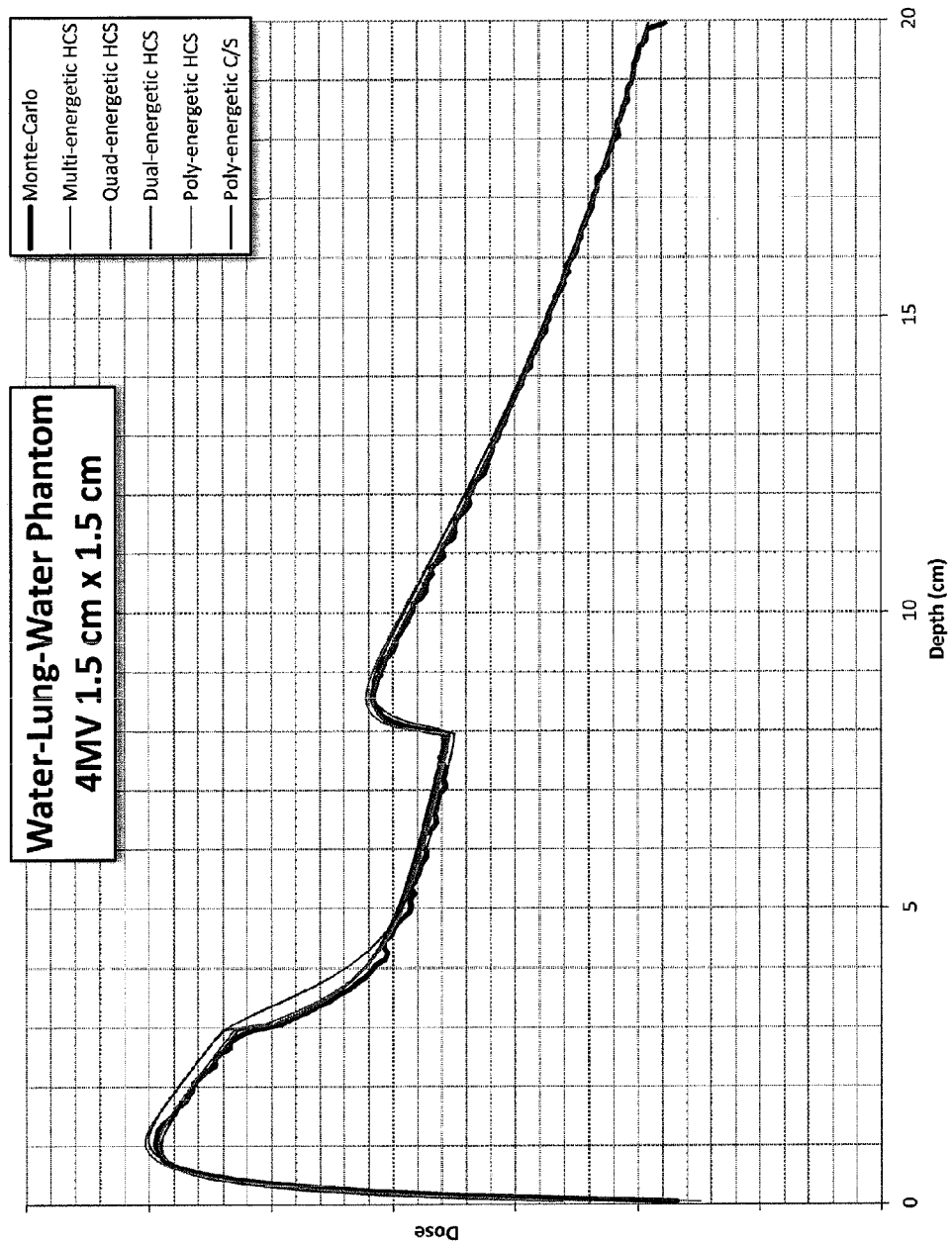
Figure 40:
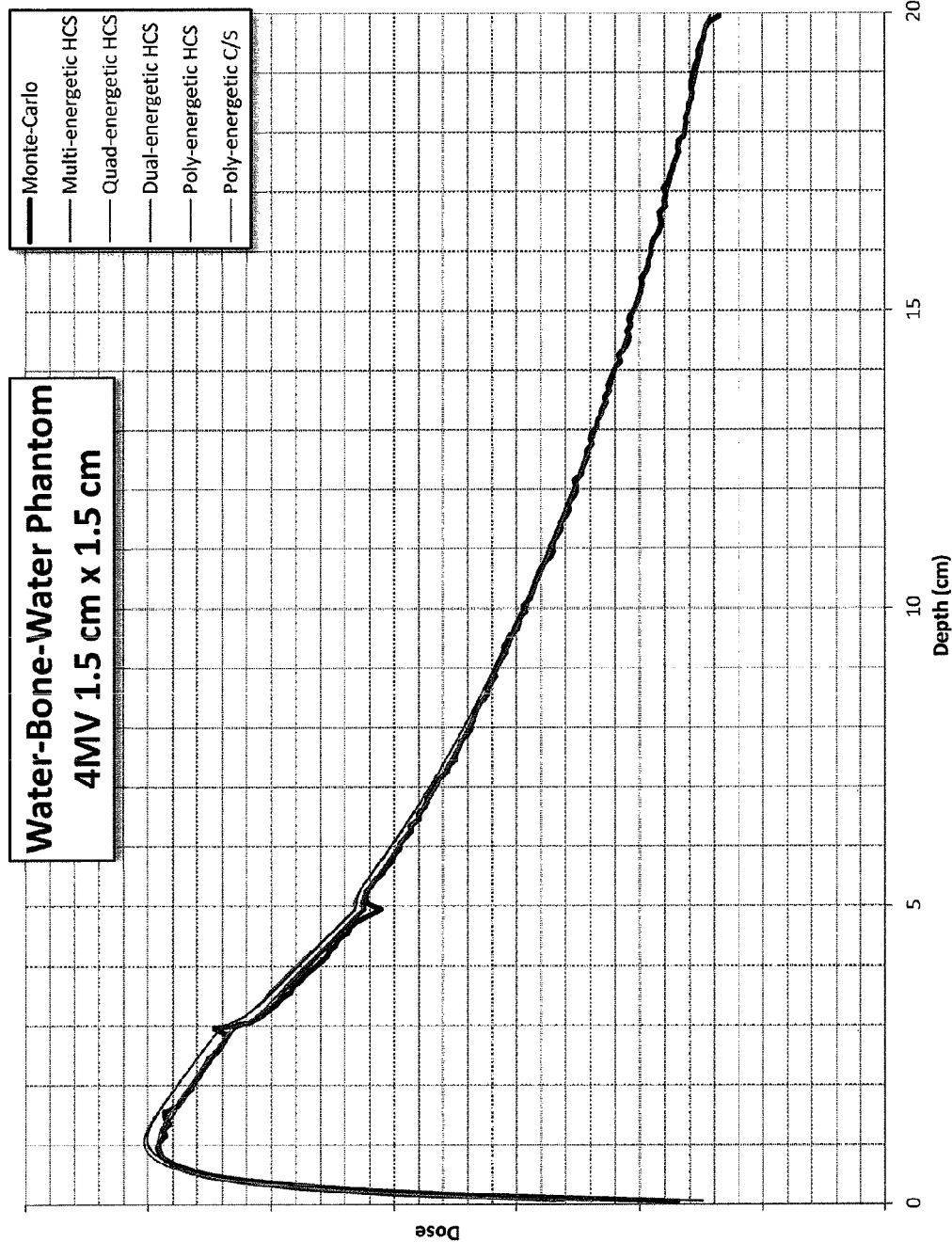
Figure 41:
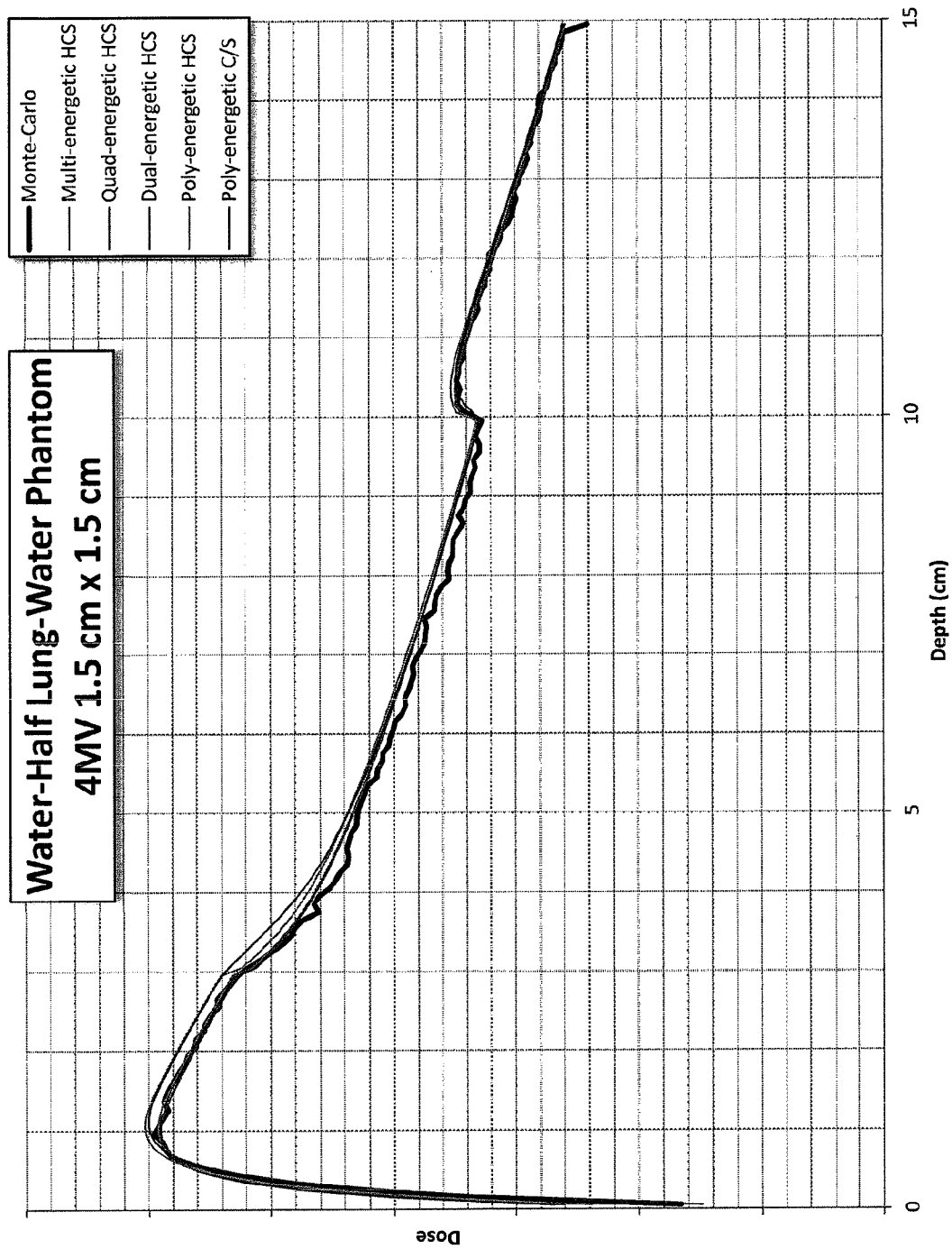
Figure 42:
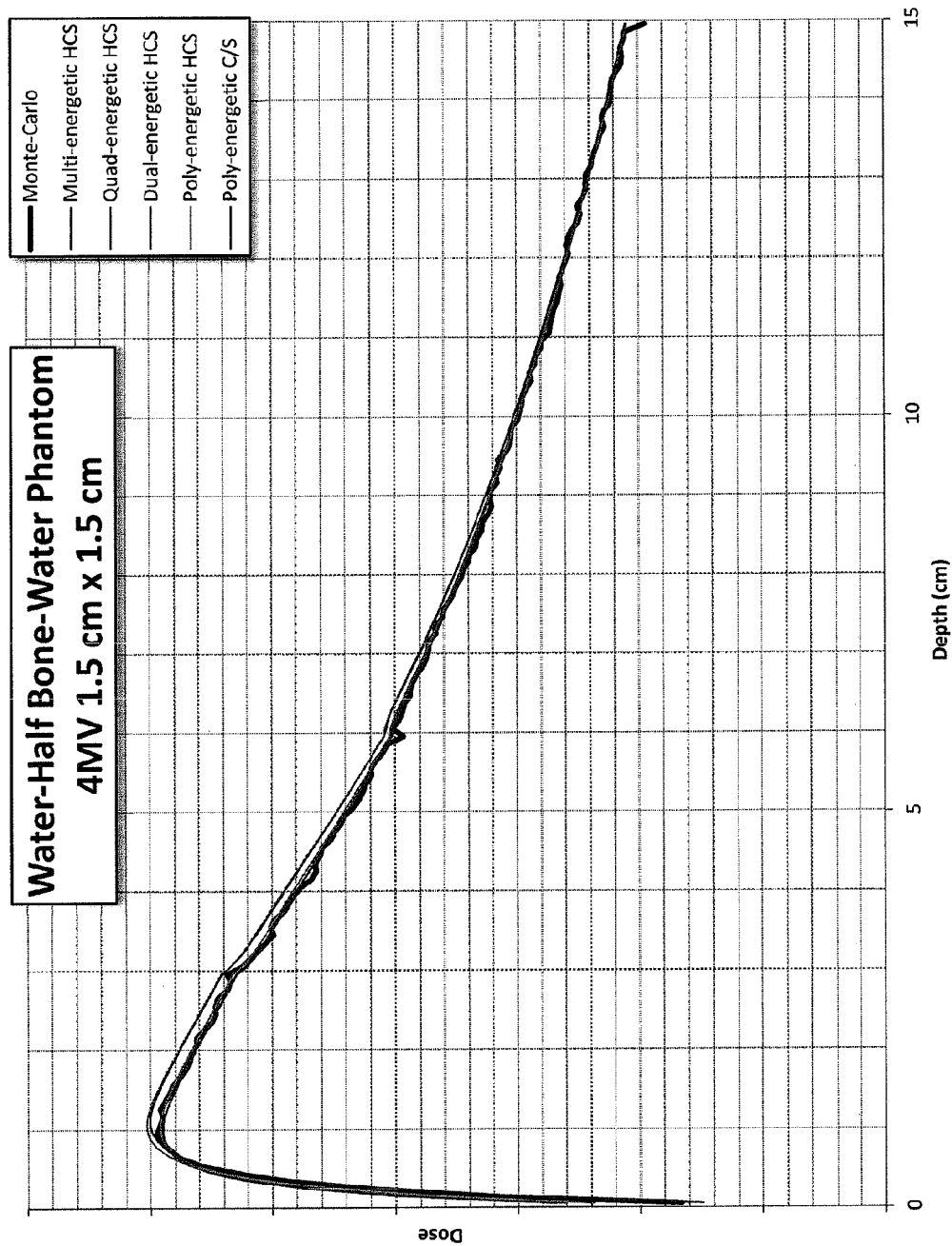

FIG. 12 illustrates a method according to another embodiment of the present invention. The method comprises obtaining input information 1201 concerning a body having an intended radiation treatment region; in box 1202, computing based on input information 1201, in a direction from said body to a source position, a physical property at a first and second sub-regions along a ray traced from the source position through the body and intersecting the body in the intended radiation treatment region, the second sub-region along the ray being closer to the source position than the first sub-region along the ray; and in box 1203, determining output information 1204 for providing radiation treatment to the intended radiation treatment region.

In box 1202, the physical property at the second sub-region is computed based on the physical property computed at the first sub-region. The physical property is directed to an attenuation factor representing a relative amount of energy being extracted from an incident radiation beam. An example is the attenuation factor as discussed above. Further, the input information 1201 may comprise empirical data from the body. The measurement data may comprise at least one computed tomography (CT) image of the intended treatment region of the body. Additionally, at least one pre-compiled look-up table may be used in box 1202.

Box 1203 further comprises a step 1205 of computing an amount of radiation energy absorbed for the intended radiation treatment region. The absorbed radiation energy may be computed using at least one of a uniform sampling, a variable sampling, a multi-resolution grid, or variants thereof to cover the intended radiation treatment region. Further, the multi-resolution grid is assigned such that the ray traced from the source position through the body may approximate a solid angle.

Yet another embodiment of the invention may comprise a computer readable medium comprising software, which software when executed by a computer, causes the computer to implement the above method.

Superposition

The convolution dose transport algorithm is based on a simple approximation: that dose, $D_C$, can be computed by convolving an energy point response function (kernel) with a patient specific energy (TERMA) distribution.

$$D_C(r) \approx \int\int\int\int_E T_E(r') \int_E K_E(r'-r)\frac{1}{\|r'-r\|^2}\,dr' \qquad (15)$$

However, this approximation was only valid in a homogenous volume with a non-realistic parallel beam. The superposition algorithm improved upon convolution by indexing into the kernel using radiological distance instead of geometric distance. This improvement was made possible by using the radial symmetry to compute the convolution in polar coordinates. The polar coordinate transform allows for kernel tilting, which better models the projection geometry of actual machines and negates the need for the distance squared term. The resolution of the coordinate transform is controlled by the number of sampling rays, v. We implement the inverse kernel formulation according to some embodiments of the current invention, which is work and cache efficient, both tilted and non-tilted kernels, and both the cumulative kernel (CK), which integrates the kernel to model the dose from a ray-segment to a point, and the cumulative-cumulative kernel (CCK), which doubly integrates the kernel to model the dose from a ray-segment to a ray-segment.

$$D_{S/C}(r) \approx \Sigma_v \int (\int_E T_E(r+tv) \int_E K_{E,v} (\int_r^{r+tv} \rho(r')dr'))dt \qquad (16)$$

Multi-Energetic Superposition

Both equations (15) and (16) contain a poly-energetic approximation. Instead of computing multiple energy specific TERMA volumes and superimposing individual mono-energetic kernels, implementations traditionally have computed a single poly-energetic TERMA volume and applied a single poly-energetic superposition. This approximation works well with manually specified spectrums that are biased to be harder than their Monte-Carlo derived counterparts. Performing a superposition with a Monte-Carlo derived spectrum results in an overestimation of dose at shallow depths. This is due to the low energy photons being superimpose by a higher energy kernel. Furthermore, the kernel and TERMA spectrums naturally diverge due to the beam hardening with depth or wedges. A technique known as Kernel Hardening attempts to correct for the depth dependent spectral changes by linearly interpolating between pre-hardened poly-energetic kernels.

To address these issues, we have vectorized the superposition algorithm. We represent each spectrum as a cumulative function that is discretized into $N_T$ and $N_{S/C}$ equally weighted energy bins using monotonic spline interpolation. We use separate discretizations for TERMA, $N_T$, and superposition, $N_{S/C}$, because TERMA can efficiently compute $N_T$ energy bins using a single ray-trace, while we limit superposition to four energy bins per ray-trace according to an embodiment of the current invention, as that is the limit of the GPU's built-in textures. For $N_{S/C}$ greater than four, we perform multiple fluence transports.

$$D_{S/C}(r) = \Sigma_v \int T(r+tv) \cdot K_v(\int_r^{r+tv} \rho(r')dr')dt \qquad (17)$$

We experimented with $N_T = \{16, 32, 64\}$ and $N_{S/C} = \{1, 2, 4, N_T\}$ as examples.

Heterogeneity Compensated Superposition

Superposition's accuracy depends greatly on the electron equilibrium of the TERMA distribution. The electron equilibrium is disturbed by simultaneous gradients in density and TERMA. This leads to significant errors near interfaces and for small or highly modulated fields. Empirically, these errors appear as an overestimation of the dose after a high-density to low-density transition and an underestimation dose after a low-density to high-density transition. From a theoretical standpoint, these errors occur because superposition models the primary electron scatter event and not all the secondary scatter collisions.

A new algorithm according to an embodiment of the current invention, heterogeneity compensated superposition, introduces a model of the secondary scatter collisions to the superposition algorithm. Instead of directly sampling the density of a given voxel in order to compute the radiological distance, we filter it by an approximation of the random walk.

$$D_{S/C}(r) = \Sigma_v \int T(r+tv) \cdot K_v(\int_r^{r+tv} \rho_{eff,r,v}(r')dr')dt \qquad (18)$$

We have chosen to use an exponential function to approximate the random walk. The exponential can provide an approximation of electron dose deposition from a directional source (in our case, the primary scatter event).

$$\rho_{eff,r,v}(r') = \int_r^{r'} \rho(r'-tv) e^{-\tau_v \rho(r)t} dt \qquad (19)$$

The exponential can also be very efficiently implemented using a linear recursive filter. Traditionally, linear recursive filters are designed for digital systems with a known, fixed step size. As exact radiological path ray tracing produces a variable step size, dt, between samples, we modified the fixed decay constant of the recursive exponential filter to be a function of dt:

$$\tau_{dt} = \max(0, 1 - \alpha dt) \qquad (20)$$

$$\rho_{eff,t+dt}(r') = (1-\tau)\rho(r') + \tau_{dt}\rho_{eff,t} \qquad (21)$$

As dt is in terms of geometric distance and an electron's random walk is dependent on radiological distance, we parameterize our filter using the density of the deposition voxel. As the dose from the voxels immediately surrounding the deposition point is less dependent on electron equilibrium and more on its raw density, we have added a term, $\beta$, to strengthen the influence of the surrounding voxel density. Furthermore, in order to properly take the effects of the surrounding neighborhood into account, $\alpha$ is updated throughout the ray trace using a second recursive filter and $\tau_\alpha$ value. We've added an angular parameter, $F_0$, to account for any possible direction sensitivity of the filter. As the amount of the disequilibrium is dependent on the difference in density, we've added density difference terms.

$$\tau_{dt,t} = \max\left(0, 1 - \alpha, dt \frac{\rho_{eff,t}}{T_0\rho(r') + \rho_{eff,t}} - \beta_t\right) \qquad (22)$$

$$\tau_{\alpha,dt,t} = \max\left(0, 1 - dt\left(D_0 + D_1\alpha_t + D_2 \frac{\rho_{eff,t+dt}}{D_3\rho(r') + \rho_{eff,t+dt}}\right)\right)$$

$$\alpha(r'') = \left(\frac{A_{-1}}{\rho(r'')} + A_0 + A_1\rho(r'') + A_2\rho(r'')^2\right)(1 + F_0\phi(v))$$

$$\alpha_{t+dt} = (1 - \tau_{\alpha,dt})\alpha(r') + \tau_{\alpha,dt,t}\alpha_t$$

$$\beta_{t+dt} = \max(0, \beta_t - \beta_1 dt(B_0(B_2 + \alpha_t) + B_3\beta_t))$$

$$\alpha_0 = \alpha(r)$$

$$\beta_0 = B_0(B_2 + \alpha_0(r))$$

To investigate this parameter space, we have used a combination of automated optimization and manual graphical review. We limited all parameters to a small non-negative number, with the exception of $F_0$, which was limited to $\pm 1/\pi$. We utilized a variety of optimization techniques and objectives. For the majority of the optimizations, we summed the squared average squared-error for a set of exemplar depth dose curves. These exemplars were the ICCR 2000, the 24MV Water-Lung-Water and 24MV Water-Low Density-Water phantom studies. These phantoms were chosen as they were the hardest to simultaneously satisfy. The error used differed from a traditional gamma metric in that it used the percent instead of the absolute dosimetric error. We used the percentage error as it did not reduce the weight of errors at depth or in low density materials. We used squared errors as it increased the weight of larger errors. We limited error averaging to a region of interest, 3 cm to 17 cm, which contained the troublesome material transitions in the exemplar phantom. For the optimizer, we eventually settled on a multi-resolution greedy-walker with restarts, as it was very work efficient and provided a list of local minima, which were used to guide manual parameter space exploration. However, the broad concepts of the current invention are not limited to this example.

$$\tau_{dt,t} = \max\left(0, 1 - \alpha_t dt \frac{\rho_{eff,t}}{\rho(r') + \rho_{eff,t}} - \beta_t\right)$$

$$\tau_{\alpha,dt,t} = \max(0, 1 - \alpha_t dt)$$

$$\alpha(r'') = 0.5 + 2\rho(r'')$$

$$\alpha_{t+dt} = (1 - \tau_{\alpha,dt})\alpha(r') + \tau_{\alpha,dt,t}\alpha_t$$

$$\beta_{t+dt} = \max(0, \beta_t(1 - 1.5dt))$$

$$\alpha_0 = \alpha(r)$$

$$\beta_0 = 0.15\alpha_0(r)$$

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for radiation therapy comprising a radiation planning system,
wherein said radiation planning system comprises a data processor adapted to:
receive information concerning an intended radiation treatment region of a body;
receive a calculated initial energy released per unit mass for a plurality of locations within said body;
compute a radiation dose at a plurality of locations within said radiation treatment region based on said calculated initial energy released per unit mass and including radiation dose contributions due to scattering from other locations within said body; and
determine radiation therapy parameters for providing radiation treatment to said intended radiation treatment region based on said radiation dose computed at said plurality of locations within said radiation treatment region,
wherein said including radiation dose contributions due to scattering from other locations within said body takes into account density discontinuities in said body,
wherein said computing said radiation dose at each of said plurality of locations within said radiation treatment region comprises an integration of said initial energy released per unit mass over said plurality of locations within said body weighted by a kernel function,
wherein said kernel function includes an empirically determined effective density function to take into account said density variations in said body, and
wherein said determining said radiation therapy parameters for providing radiation treatment to said intended radiation treatment region is sufficiently fast to be performed in real-time during a radiation treatment procedure.

2. A system for radiation therapy according to claim 1, wherein said density discontinuities in said body that are taken into account in said computing include interfaces between different types of matter within said body.

3. A system for radiation therapy according to claim 2, wherein said interfaces between different types of matter within said body comprise an interface between at least two of bone, tissue, an internal organ, air, water and an artificial implant.

4. A system for radiation therapy according to claim 1, wherein said integration is for a first radiation beam energy,
wherein said computing said radiation dose at each of said plurality of locations within said radiation treatment region further comprises a second integration of said initial energy released per unit mass over said plurality of locations within said body weighted by a kernel function for a second radiation beam energy, and
wherein said computing said radiation dose at each of said plurality of locations within said radiation treatment region further comprises adding said first and second integrations.

5. A system for radiation therapy according to claim 1, further comprising, prior to said receiving said calculated initial energy released per unit mass for a plurality of locations within said body, calculating said initial energy released per unit mass to be provided in said receiving.

6. A system for radiation therapy according to claim 5, wherein said calculating said initial energy released per unit mass comprises a back-projected ray tracing calculation.

7. A system for radiation therapy according to claim 4, further comprising, prior to said receiving said calculated initial energy released per unit mass for a plurality of locations within said body, calculating said initial energy released per unit mass to be provided in said receiving.

8. A system for radiation therapy according to claim 7, wherein said calculating said initial energy released per unit mass comprises a back-projected ray tracing calculation.

9. A system for radiation therapy according to claim 1, wherein said initial energy released per unit mass is at least one of a TERMA, KERMA or SCERMA.

10. A method for determining radiation therapy parameters for radiation treatment, comprising:
receiving information concerning an intended radiation treatment region of a body;
receiving a calculated initial energy released per unit mass for a plurality of locations within said body;
computing a radiation dose at a plurality of locations within said radiation treatment region based on said calculated initial energy released per unit mass and including radiation dose contributions due to scattering from other locations within said body; and
determining said radiation therapy parameters for providing said radiation treatment to said intended radiation treatment region based on said radiation dose computed at said plurality of locations within said radiation treatment region,
wherein said including radiation dose contributions due to scattering from other locations within said body takes into account density variations in said body,
wherein said computing said radiation dose at each of said plurality of locations within said radiation treatment region comprises an integration of said initial energy released per unit mass over said plurality of locations within said body weighted by a kernel function,
wherein said kernel function includes an empirically determined effective density function to take into account said density variations in said body, and
wherein said determining said radiation therapy parameters for providing radiation treatment to said intended radiation treatment region is sufficiently fast to be performed in real-time during a radiation treatment procedure.

11. A method for determining radiation therapy parameters according to claim 10, wherein said density variations in said body that are taken into account in said computing include interfaces between different types of matter within said body.

12. A method for determining radiation therapy parameters according to claim 11, wherein said interfaces between different types of matter within said body comprise an interface between at least two of bone, tissue, an internal organ, air, water and an artificial implant.

13. A method for determining radiation therapy parameters according to claim 10, wherein said integration is for a first radiation beam energy,
wherein said computing said radiation dose at each of said plurality of locations within said radiation treatment region further comprises a second integration of said initial energy released per unit mass over said plurality of locations within said body weighted by a kernel function for a second radiation beam energy, and wherein said computing said radiation dose at each of said plurality of locations within said radiation treatment region further comprises adding said first and second integrations.

14. A method for determining radiation therapy parameters according to claim 10, further comprising, prior to said receiving said calculated initial energy released per unit mass for a plurality of locations within said body, calculating said initial energy released per unit mass to be provided in said receiving.

15. A method for determining radiation therapy parameters according to claim 14, wherein said calculating said initial energy released per unit mass comprises a back-projected ray tracing calculation.

16. A method for determining radiation therapy parameters according to claim 13, further comprising, prior to said receiving said calculated initial energy released per unit mass for a plurality of locations within said body, calculating said initial energy released per unit mass to be provided in said receiving.

17. A method for determining radiation therapy parameters according to claim 16, wherein said calculating said initial energy released per unit mass comprises a back-projected ray tracing calculation.

18. A method for determining radiation therapy parameters according to claim 10, wherein said initial energy released per unit mass is at least one of a TERMA, KERMA or SCERMA.

19. A computer readable medium, containing non-transitory executable code, which non-transitory executable code when executed by a computer, causes the computer to:
receive information concerning an intended radiation treatment region of a body;
receive a calculated initial energy released per unit mass for a plurality of locations within said body;
compute a radiation dose at a plurality of locations within said radiation treatment region based on said calculated initial energy released per unit mass and including radiation dose contributions due to scattering from other locations within said body; and
determine radiation therapy parameters for providing radiation treatment to said intended radiation treatment region based on said radiation dose computed at said plurality of locations within said radiation treatment region,
wherein said including radiation dose contributions due to scattering from other locations within said body takes into account density discontinuities in said body,
wherein said computing said radiation dose at each of said plurality of locations within said radiation treatment region comprises an integration of said initial energy released per unit mass over said plurality of locations within said body weighted by a kernel function,
wherein said kernel function includes an empirically determined effective density function to take into account said density variations in said body, and
wherein said determining said radiation therapy parameters for providing radiation treatment to said intended radiation treatment region is sufficiently fast to be performed in real-time during a radiation treatment procedure.

20. A computer readable medium according to claim 19, wherein said density discontinuities in said body that are taken into account in said computing include interfaces between different types of matter within said body.

21. A computer readable medium according to claim 20, wherein said interfaces between different types of matter within said body comprise an interface between at least two of bone, tissue, an internal organ, air, water and an artificial implant.

22. A computer readable medium according to claim 19, wherein said integration is for a first radiation beam energy,
wherein said computing said radiation dose at each of said plurality of locations within said radiation treatment region further comprises a second integration of said initial energy released per unit mass over said plurality of locations within said body weighted by a kernel function for a second radiation beam energy, and
wherein said computing said radiation dose at each of said plurality of locations within said radiation treatment region further comprises adding said first and second integrations.

23. A computer readable medium according to claim 19, further comprising, prior to said receiving said calculated initial energy released per unit mass for a plurality of locations within said body, calculating said initial energy released per unit mass to be provided in said receiving.

24. A computer readable medium according to claim 23, wherein said calculating said initial energy released per unit mass comprises a back-projected ray tracing calculation.

25. A computer readable medium according to claim 22, further comprising, prior to said receiving said calculated initial energy released per unit mass for a plurality of locations within said body, calculating said initial energy released per unit mass to be provided in said receiving.

26. A computer readable medium according to claim 25, wherein said calculating said initial energy released per unit mass comprises a back-projected ray tracing calculation.

27. A computer readable medium according to claim 19, wherein said initial energy released per unit mass is at least one of a TERMA, KERMA or SCERMA.

* * * * *